United States Patent
Tayeb et al.

(10) Patent No.: US 12,201,519 B2
(45) Date of Patent: *Jan. 21, 2025

(54) PROSTHETIC VALVE

(71) Applicant: Edwards Lifesciences Corporation, Irvine, CA (US)

(72) Inventors: Liron Tayeb, Peduel (IL); Tamir S. Levi, Zikhron Yaakov (IL)

(73) Assignee: EDWARDS LIFESCIENCES CORPORATION, Irvine, CA (US)

(*) Notice: Subject to any disclaimer, the term of this patent is extended or adjusted under 35 U.S.C. 154(b) by 784 days.

This patent is subject to a terminal disclaimer.

(21) Appl. No.: 17/359,964

(22) Filed: Jun. 28, 2021

(65) Prior Publication Data
US 2021/0322162 A1 Oct. 21, 2021

Related U.S. Application Data

(63) Continuation of application No. PCT/US2020/014701, filed on Jan. 23, 2020.
(Continued)

(51) Int. Cl.
*A61F 2/24* (2006.01)

(52) U.S. Cl.
CPC ............ *A61F 2/2418* (2013.01); *A61F 2/243* (2013.01)

(58) Field of Classification Search
CPC . A61F 2/2418; A61F 2/243; A61F 2250/0069
See application file for complete search history.

(56) References Cited

U.S. PATENT DOCUMENTS 3,409,013 A 11/1968 Berry
3,548,417 A 12/1970 Kisher
(Continued)

FOREIGN PATENT DOCUMENTS

DE 0144167 C 9/1903
DE 2246526 A1 3/1973
(Continued)

OTHER PUBLICATIONS

H.R. Andersen, et al. "Transluminal Implantation of Artificial Heart Valve. Description of a New Expandable Aortic Valve and Initial Results with implantation by Catheter Technique in Closed Chest Pig," European Heart Journal, No. 13. pp. 704-708. 1992.
(Continued)

*Primary Examiner* — Sarah W Aleman
*Assistant Examiner* — Rachel S Highland
(74) *Attorney, Agent, or Firm* — Klarquist Sparkman. LLP; Sean Seung Kyu Kim

(57) ABSTRACT

A prosthetic valve includes an annular frame and a skirt. The frame is radially expandable and compressible between a radially compressed configuration and a radially expanded configuration. The skirt has a fold around an inflow end of the frame so as to cover at least a portion of an outer surface of the frame and at least a portion of an inner surface of the frame. When the frame is in the radially expanded configuration, an outer portion of the skirt tightly conforms to the outer surface of the frame and the inflow end of the frame is axially spaced from the fold to form an axially extending gap between the frame and the fold. When the frame is in the radially compressed configuration, the inflow end of the frame extends axially so as to at least partially fill the axially extending gap.

20 Claims, 8 Drawing Sheets

Related U.S. Application Data

(60) Provisional application No. 62/797,837, filed on Jan. 28, 2019.

(56) References Cited

U.S. PATENT DOCUMENTS

| | | |
|---|---|---|
| 3,587,115 A | 6/1971 | Shiley |
| 3,657,744 A | 4/1972 | Ersek |
| 3,671,979 A | 6/1972 | Moulopoulos |
| 3,714,671 A | 2/1973 | Edwards et al. |
| 3,755,823 A | 9/1973 | Hancock |
| 4,035,849 A | 7/1977 | Angell et al. |
| 4,056,854 A | 11/1977 | Boretos et al. |
| 4,106,129 A | 8/1978 | Carpentier et al. |
| 4,222,126 A | 9/1980 | Boretos et al. |
| 4,265,694 A | 5/1981 | Boretos et al. |
| 4,297,749 A | 11/1981 | Davis et al. |
| RE30,912 E | 4/1982 | Hancock |
| 4,339,831 A | 7/1982 | Johnson |
| 4,343,048 A | 8/1982 | Ross et al. |
| 4,345,340 A | 8/1982 | Rosen |
| 4,373,216 A | 2/1983 | Klawitter |
| 4,406,022 A | 9/1983 | Roy |
| 4,441,216 A | 4/1984 | Ionescu et al. |
| 4,470,157 A | 9/1984 | Love |
| 4,535,483 A | 8/1985 | Klawitter et al. |
| 4,574,803 A | 3/1986 | Storz |
| 4,592,340 A | 6/1986 | Boyles |
| 4,605,407 A | 8/1986 | Black et al. |
| 4,612,011 A | 9/1986 | Kautzky |
| 4,643,732 A | 2/1987 | Pietsch et al. |
| 4,655,771 A | 4/1987 | Wallsten |
| 4,692,164 A | 9/1987 | Dzemeshkevich et al. |
| 4,733,665 A | 3/1988 | Palmaz |
| 4,759,758 A | 7/1988 | Gabbay |
| 4,762,128 A | 8/1988 | Rosenbluth |
| 4,777,951 A | 10/1988 | Cribier et al. |
| 4,787,899 A | 11/1988 | Lazarus |
| 4,787,901 A | 11/1988 | Baykut |
| 4,796,629 A | 1/1989 | Grayzel |
| 4,820,299 A | 4/1989 | Philippe et al. |
| 4,829,990 A | 5/1989 | Thuroff et al. |
| 4,851,001 A | 7/1989 | Taheri |
| 4,856,516 A | 8/1989 | Hillstead |
| 4,878,495 A | 11/1989 | Grayzel |
| 4,878,906 A | 11/1989 | Lindemann et al. |
| 4,883,458 A | 11/1989 | Shiber |
| 4,922,905 A | 5/1990 | Strecker |
| 4,966,604 A | 10/1990 | Reiss |
| 4,979,939 A | 12/1990 | Shiber |
| 4,986,830 A | 1/1991 | Owens et al. |
| 4,994,077 A | 2/1991 | Dobben |
| 5,007,896 A | 4/1991 | Shiber |
| 5,026,366 A | 6/1991 | Leckrone |
| 5,032,128 A | 7/1991 | Alonso |
| 5,037,434 A | 8/1991 | Lane |
| 5,047,041 A | 9/1991 | Samuels |
| 5,059,177 A | 10/1991 | Towne et al. |
| 5,080,668 A | 1/1992 | Bolz et al. |
| 5,085,635 A | 2/1992 | Cragg |
| 5,089,015 A | 2/1992 | Ross |
| 5,152,771 A | 10/1992 | Sabbaghian et al. |
| 5,163,953 A | 11/1992 | Vince |
| 5,167,628 A | 12/1992 | Boyles |
| 5,192,297 A | 3/1993 | Hull |
| 5,266,073 A | 11/1993 | Wall |
| 5,282,847 A | 2/1994 | Trescony et al. |
| 5,295,958 A | 3/1994 | Shturman |
| 5,332,402 A | 7/1994 | Teitelbaum |
| 5,360,444 A | 11/1994 | Kusuhara |
| 5,370,685 A | 12/1994 | Stevens |
| 5,397,351 A | 3/1995 | Pavcnik et al. |
| 5,411,055 A | 5/1995 | Kane |
| 5,411,552 A | 5/1995 | Andersen et al. |
| 5,443,446 A | 8/1995 | Shturman |
| 5,480,424 A | 1/1996 | Cox |
| 5,500,014 A | 3/1996 | Quijano et al. |
| 5,545,209 A | 8/1996 | Roberts et al. |
| 5,545,214 A | 8/1996 | Stevens |
| 5,549,665 A | 8/1996 | Vesely et al. |
| 5,554,185 A | 9/1996 | Block et al. |
| 5,558,644 A | 9/1996 | Boyd et al. |
| 5,571,175 A | 11/1996 | Vanney et al. |
| 5,584,803 A | 12/1996 | Stevens et al. |
| 5,591,185 A | 1/1997 | Kilmer et al. |
| 5,591,195 A | 1/1997 | Taheri et al. |
| 5,607,464 A | 3/1997 | Trescony et al. |
| 5,609,626 A | 3/1997 | Quijano et al. |
| 5,628,792 A | 5/1997 | Lentell |
| 5,639,274 A | 6/1997 | Fischell et al. |
| 5,665,115 A | 9/1997 | Cragg |
| 5,716,417 A | 2/1998 | Girard et al. |
| 5,728,068 A | 3/1998 | Leone et al. |
| 5,749,890 A | 5/1998 | Shaknovich |
| 5,756,476 A | 5/1998 | Epstein et al. |
| 5,769,812 A | 6/1998 | Stevens et al. |
| 5,800,508 A | 9/1998 | Goicoechea et al. |
| 5,840,081 A | 11/1998 | Andersen et al. |
| 5,855,597 A | 1/1999 | Jayaraman |
| 5,855,601 A | 1/1999 | Bessler et al. |
| 5,855,602 A | 1/1999 | Angell |
| 5,925,063 A | 7/1999 | Khosravi |
| 5,957,949 A | 9/1999 | Leonhardt et al. |
| 6,027,525 A | 2/2000 | Suh et al. |
| 6,132,473 A | 10/2000 | Williams et al. |
| 6,168,614 B1 | 1/2001 | Andersen et al. |
| 6,171,335 B1 | 1/2001 | Wheatley et al. |
| 6,174,327 B1 | 1/2001 | Mertens et al. |
| 6,210,408 B1 | 4/2001 | Chandrasekaran et al. |
| 6,217,585 B1 | 4/2001 | Houser et al. |
| 6,221,091 B1 | 4/2001 | Khosravi |
| 6,231,602 B1 | 5/2001 | Carpentier et al. |
| 6,245,102 B1 | 6/2001 | Jayaraman |
| 6,299,637 B1 | 10/2001 | Shaolian et al. |
| 6,302,906 B1 | 10/2001 | Goicoechea et al. |
| 6,338,740 B1 | 1/2002 | Carpentier |
| 6,350,277 B1 | 2/2002 | Kocur |
| 6,352,547 B1 | 3/2002 | Brown et al. |
| 6,425,916 B1 | 7/2002 | Garrison et al. |
| 6,440,764 B1 | 8/2002 | Focht et al. |
| 6,454,799 B1 | 9/2002 | Schreck |
| 6,458,153 B1 | 10/2002 | Bailey et al. |
| 6,461,382 B1 | 10/2002 | Cao |
| 6,468,660 B2 | 10/2002 | Ogle et al. |
| 6,482,228 B1 | 11/2002 | Norred |
| 6,488,704 B1 | 12/2002 | Connelly et al. |
| 6,527,979 B2 | 3/2003 | Constantz et al. |
| 6,569,196 B1 | 5/2003 | Vesely |
| 6,582,462 B1 | 6/2003 | Andersen et al. |
| 6,605,112 B1 | 8/2003 | Moll et al. |
| 6,652,578 B2 | 11/2003 | Bailey et al. |
| 6,689,123 B2 | 2/2004 | Pinchasik |
| 6,716,244 B2 | 4/2004 | Klaco |
| 6,730,118 B2 | 5/2004 | Spenser et al. |
| 6,733,525 B2 | 5/2004 | Yang et al. |
| 6,767,362 B2 | 7/2004 | Schreck |
| 6,769,161 B2 | 8/2004 | Brown et al. |
| 6,783,542 B2 | 8/2004 | Eidenschink |
| 6,830,584 B1 | 12/2004 | Seguin |
| 6,878,162 B2 | 4/2005 | Bales et al. |
| 6,893,460 B2 | 5/2005 | Spenser et al. |
| 6,908,481 B2 | 6/2005 | Cribier |
| 6,936,067 B2 | 8/2005 | Buchanan |
| 7,018,406 B2 | 3/2006 | Seguin et al. |
| 7,018,408 B2 | 3/2006 | Bailey et al. |
| 7,096,554 B2 | 8/2006 | Austin et al. |
| 7,225,518 B2 | 6/2007 | Eidenschink et al. |
| 7,276,078 B2 | 10/2007 | Spenser et al. |
| 7,276,084 B2 | 10/2007 | Yang et al. |
| 7,316,710 B1 | 1/2008 | Cheng et al. |
| 7,318,278 B2 | 1/2008 | Zhang et al. |
| 7,374,571 B2 | 5/2008 | Pease et al. |
| 7,393,360 B2 | 7/2008 | Spenser et al. |
| 7,462,191 B2 | 12/2008 | Spenser et al. |
| 7,510,575 B2 | 3/2009 | Spenser et al. |

(56) References Cited

U.S. PATENT DOCUMENTS

| | | |
|---|---|---|
| 7,563,280 B2 | 7/2009 | Anderson et al. |
| 7,585,321 B2 | 9/2009 | Cribier |
| 7,618,446 B2 | 11/2009 | Andersen et al. |
| 7,618,447 B2 | 11/2009 | Case et al. |
| 7,655,034 B2 | 2/2010 | Mitchell et al. |
| 7,785,366 B2 | 8/2010 | Maurer et al. |
| 7,959,665 B2 | 6/2011 | Pienknagura |
| 7,959,672 B2 | 6/2011 | Salahieh et al. |
| 7,993,394 B2 | 8/2011 | Hariton et al. |
| 8,029,556 B2 | 10/2011 | Rowe |
| 8,075,611 B2 | 12/2011 | Millwee et al. |
| 8,128,686 B2 | 3/2012 | Paul, Jr. et al. |
| 8,167,932 B2 | 5/2012 | Bourang et al. |
| 8,291,570 B2 | 10/2012 | Fidenschink et al. |
| 8,348,998 B2 | 1/2013 | Pintor et al. |
| 8,449,606 B2 | 5/2013 | Eliasen et al. |
| 8,454,685 B2 | 6/2013 | Hariton et al. |
| 8,652,203 B2 | 2/2014 | Quadri et al. |
| 8,685,055 B2 | 4/2014 | VanTassel et al. |
| 8,747,463 B2 | 6/2014 | Fogarty et al. |
| 9,078,781 B2 | 7/2015 | Ryan et al. |
| 2001/0021872 A1 | 9/2001 | Bailey et al. |
| 2002/0026094 A1 | 2/2002 | Roth |
| 2002/0032481 A1 | 3/2002 | Gabbay |
| 2002/0138135 A1 | 9/2002 | Duerig et al. |
| 2002/0143390 A1 | 10/2002 | Ishii |
| 2002/0173842 A1 | 11/2002 | Buchanan |
| 2003/0014105 A1 | 1/2003 | Cao |
| 2003/0040791 A1 | 2/2003 | Oktay |
| 2003/0050694 A1 | 3/2003 | Yang et al. |
| 2003/0100939 A1 | 5/2003 | Yodfat et al. |
| 2003/0158597 A1 | 8/2003 | Quiachon et al. |
| 2003/0212454 A1 | 11/2003 | Scott et al. |
| 2004/0024452 A1 | 2/2004 | Kruse et al. |
| 2004/0039436 A1 | 2/2004 | Spenser et al. |
| 2004/0078074 A1 | 4/2004 | Anderson et al. |
| 2004/0186558 A1 | 9/2004 | Pavcnik et al. |
| 2004/0186563 A1 | 9/2004 | Lobbi |
| 2004/0186565 A1 | 9/2004 | Schreck |
| 2004/0260389 A1 | 12/2004 | Case et al. |
| 2005/0010285 A1 | 1/2005 | Lambrecht et al. |
| 2005/0075725 A1 | 4/2005 | Rowe |
| 2005/0075728 A1 | 4/2005 | Nguyen et al. |
| 2005/0096736 A1 | 5/2005 | Osse et al. |
| 2005/0096738 A1 | 5/2005 | Cali et al. |
| 2005/0137682 A1* | 6/2005 | Justino .................. A61F 2/2418 623/2.14 |
| 2005/0137686 A1 | 6/2005 | Salahieh et al. |
| 2005/0188525 A1 | 9/2005 | Weber et al. |
| 2005/0203614 A1 | 9/2005 | Forster et al. |
| 2005/0203617 A1 | 9/2005 | Forster et al. |
| 2005/0234546 A1 | 10/2005 | Nugent et al. |
| 2006/0004469 A1 | 1/2006 | Sokel |
| 2006/0025857 A1 | 2/2006 | Bergheim et al. |
| 2006/0058872 A1 | 3/2006 | Salahieh et al. |
| 2006/0074484 A1 | 4/2006 | Huber |
| 2006/0108090 A1 | 5/2006 | Ederer et al. |
| 2006/0149350 A1 | 7/2006 | Patel et al. |
| 2006/0183383 A1 | 8/2006 | Asmus et al. |
| 2006/0229719 A1 | 10/2006 | Marquez et al. |
| 2006/0259136 A1 | 11/2006 | Nguyen et al. |
| 2006/0259137 A1 | 11/2006 | Artof et al. |
| 2006/0287717 A1 | 12/2006 | Rowe et al. |
| 2007/0005131 A1 | 1/2007 | Taylor |
| 2007/0010876 A1 | 1/2007 | Salahieh et al. |
| 2007/0010877 A1 | 1/2007 | Salahieh et al. |
| 2007/0112422 A1 | 5/2007 | Dehdashtian |
| 2007/0162102 A1 | 7/2007 | Ryan et al. |
| 2007/0203503 A1 | 8/2007 | Salahieh et al. |
| 2007/0203575 A1 | 8/2007 | Forster et al. |
| 2007/0203576 A1 | 8/2007 | Lee et al. |
| 2007/0208550 A1 | 9/2007 | Cao et al. |
| 2007/0213813 A1 | 9/2007 | Von Segesser et al. |
| 2007/0233228 A1 | 10/2007 | Eberhardt et al. |
| 2007/0260305 A1 | 11/2007 | Drews et al. |
| 2007/0265700 A1 | 11/2007 | Eliasen et al. |
| 2008/0021546 A1 | 1/2008 | Patz et al. |
| 2008/0114442 A1 | 5/2008 | Mitchell et al. |
| 2008/0125853 A1 | 5/2008 | Bailey et al. |
| 2008/0154355 A1 | 6/2008 | Benichou et al. |
| 2008/0183271 A1 | 7/2008 | Frawley et al. |
| 2008/0208327 A1 | 8/2008 | Rowe |
| 2008/0243245 A1 | 10/2008 | Thambar et al. |
| 2008/0255660 A1 | 10/2008 | Guyenot et al. |
| 2008/0275537 A1 | 11/2008 | Limon |
| 2008/0294248 A1 | 11/2008 | Yang et al. |
| 2009/0118826 A1 | 5/2009 | Khaghani |
| 2009/0125118 A1 | 5/2009 | Gong |
| 2009/0157175 A1 | 6/2009 | Benichou |
| 2009/0276040 A1 | 11/2009 | Rowe et al. |
| 2009/0281619 A1 | 11/2009 | Le et al. |
| 2009/0287296 A1 | 11/2009 | Manasse |
| 2009/0287299 A1 | 11/2009 | Tabor et al. |
| 2009/0299452 A1 | 12/2009 | Eidenschink et al. |
| 2009/0319037 A1 | 12/2009 | Rowe et al. |
| 2010/0004735 A1 | 1/2010 | Yang et al. |
| 2010/0049313 A1 | 2/2010 | Alon et al. |
| 2010/0082094 A1 | 4/2010 | Quadri et al. |
| 2010/0100176 A1 | 4/2010 | Elizondo et al. |
| 2010/0168844 A1 | 7/2010 | Toomes et al. |
| 2010/0185277 A1 | 7/2010 | Braido et al. |
| 2010/0198347 A1 | 8/2010 | Zakay et al. |
| 2010/0204781 A1 | 8/2010 | Alkhatib |
| 2011/0015729 A1 | 1/2011 | Jimenez et al. |
| 2011/0022157 A1 | 1/2011 | Essinger et al. |
| 2011/0066224 A1 | 3/2011 | White |
| 2011/0137397 A1 | 6/2011 | Chau et al. |
| 2011/0218619 A1 | 9/2011 | Benichou et al. |
| 2011/0319991 A1 | 12/2011 | Hariton et al. |
| 2012/0030090 A1 | 2/2012 | Johnston et al. |
| 2012/0089223 A1 | 4/2012 | Nguyen et al. |
| 2012/0101571 A1 | 4/2012 | Thambar et al. |
| 2012/0123529 A1 | 5/2012 | Levi et al. |
| 2012/0259409 A1 | 10/2012 | Nguyen et al. |
| 2013/0023985 A1 | 1/2013 | Khairkhahan et al. |
| 2013/0046373 A1 | 2/2013 | Cartledge et al. |
| 2013/0150956 A1 | 6/2013 | Yohanan et al. |
| 2013/0166017 A1 | 6/2013 | Cartledge et al. |
| 2013/0190857 A1 | 7/2013 | Mitra et al. |
| 2013/0274873 A1 | 10/2013 | Delaloye et al. |
| 2013/0310926 A1 | 11/2013 | Hariton |
| 2013/0317598 A1 | 11/2013 | Rowe et al. |
| 2013/0331929 A1 | 12/2013 | Mitra et al. |
| 2014/0194981 A1 | 7/2014 | Menk et al. |
| 2014/0200661 A1 | 7/2014 | Pintor et al. |
| 2014/0209238 A1 | 7/2014 | Bonyuet et al. |
| 2014/0222136 A1 | 8/2014 | Geist et al. |
| 2014/0228945 A1* | 8/2014 | Valdez .................. A61F 2/2412 623/2.18 |
| 2014/0277417 A1 | 9/2014 | Schraut et al. |
| 2014/0277419 A1 | 9/2014 | Garde et al. |
| 2014/0277424 A1 | 9/2014 | Oslund |
| 2014/0277563 A1* | 9/2014 | White .................. A61F 2/2418 623/23.7 |
| 2014/0296962 A1 | 10/2014 | Cartledge et al. |
| 2014/0330372 A1 | 11/2014 | Weston et al. |
| 2014/0343670 A1 | 11/2014 | Bakis et al. |
| 2014/0343671 A1 | 11/2014 | Yohanan et al. |
| 2014/0350667 A1 | 11/2014 | Braido et al. |
| 2015/0073545 A1 | 3/2015 | Braido |
| 2015/0073546 A1 | 3/2015 | Braido |
| 2015/0135506 A1 | 5/2015 | White |
| 2015/0142100 A1* | 5/2015 | Morriss .................. A61F 2/2409 623/2.4 |
| 2015/0157455 A1 | 6/2015 | Hoang et al. |
| 2015/0320556 A1* | 11/2015 | Levi ...................... A61F 2/2412 29/515 |
| 2016/0317305 A1* | 11/2016 | Pelled .................. A61F 2/2412 |
| 2016/0374802 A1 | 12/2016 | Levi et al. |
| 2017/0014229 A1* | 1/2017 | Nguyen-Thien-Nhon .................. A61F 2/2418 |
| 2017/0049566 A1* | 2/2017 | Zeng .................... A61F 2/2418 |
| 2017/0189174 A1* | 7/2017 | Braido .................. A61F 2/2436 |
| 2018/0028310 A1 | 2/2018 | Gurovich et al. |

(56) References Cited

U.S. PATENT DOCUMENTS

| | | | |
|---|---|---|---|
| 2018/0153689 A1* | 6/2018 | Maimon | A61F 2/2418 |
| 2018/0206982 A1* | 7/2018 | Haivatov | A61F 2/2409 |
| 2018/0325665 A1 | 11/2018 | Gurovich et al. | |
| 2018/0344456 A1 | 12/2018 | Barash et al. | |
| 2019/0159894 A1 | 5/2019 | Levi et al. | |
| 2019/0192288 A1 | 6/2019 | Levi et al. | |
| 2019/0192289 A1 | 6/2019 | Levi et al. | |

FOREIGN PATENT DOCUMENTS

| | | |
|---|---|---|
| DE | 19532846 A1 | 3/1997 |
| DE | 19546692 A1 | 6/1997 |
| DE | 19857887 A1 | 7/2000 |
| DE | 19907646 A1 | 8/2000 |
| DE | 10049812 A1 | 4/2002 |
| DE | 10049813 C1 | 4/2002 |
| DE | 10049814 A1 | 4/2002 |
| DE | 10049815 A1 | 4/2002 |
| EP | 0103546 A1 | 3/1984 |
| EP | 0850607 A1 | 7/1998 |
| EP | 1057460 A1 | 12/2000 |
| EP | 1088529 A2 | 4/2001 |
| EP | 1570809 A1 | 9/2005 |
| FR | 2788217 A1 | 7/2000 |
| FR | 2815844 A1 | 5/2002 |
| GB | 2056023 A | 3/1981 |
| SU | 1271508 A1 | 11/1986 |
| WO | 9117720 A1 | 11/1991 |
| WO | 9217118 A1 | 10/1992 |
| WO | 9301768 A1 | 2/1993 |
| WO | 9724080 A1 | 7/1997 |
| WO | 9829057 A1 | 7/1998 |
| WO | 9930646 A1 | 6/1999 |
| WO | 9933414 A1 | 7/1999 |
| WO | 9940964 A1 | 8/1999 |
| WO | 9947075 A1 | 9/1999 |
| WO | 0018333 A1 | 4/2000 |
| WO | 0041652 A1 | 7/2000 |
| WO | 0135878 A2 | 5/2001 |
| WO | 0149213 A2 | 7/2001 |
| WO | 0154624 A1 | 8/2001 |
| WO | 0154625 A1 | 8/2001 |
| WO | 0162189 A1 | 8/2001 |
| WO | 0047139 A9 | 9/2001 |
| WO | 0164137 A1 | 9/2001 |
| WO | 0176510 A2 | 10/2001 |
| WO | 0222054 | 3/2002 |
| WO | 0236048 A1 | 5/2002 |
| WO | 0241789 A2 | 5/2002 |
| WO | 0243620 A1 | 6/2002 |
| WO | 0247575 A2 | 6/2002 |
| WO | 0249540 A2 | 6/2002 |
| WO | 03047468 | 6/2003 |
| WO | 2005034812 A1 | 4/2005 |
| WO | 2005055883 A1 | 6/2005 |
| WO | 2005084595 A1 | 9/2005 |
| WO | 2006014233 A2 | 2/2006 |
| WO | 2006032051 A2 | 3/2006 |
| WO | 2006034008 A2 | 3/2006 |
| WO | 2006111391 A1 | 10/2006 |
| WO | 2006127089 A1 | 11/2006 |
| WO | 2006138173 A2 | 12/2006 |
| WO | 2005102015 A3 | 4/2007 |
| WO | 2007047488 A2 | 4/2007 |
| WO | 2007067942 A1 | 6/2007 |
| WO | 2007097983 A2 | 8/2007 |
| WO | 2008005405 A2 | 1/2008 |
| WO | 2008015257 A2 | 2/2008 |
| WO | 2008035337 A2 | 3/2008 |
| WO | 2008091515 A2 | 7/2008 |
| WO | 2008147964 A1 | 12/2008 |
| WO | 2008150529 A1 | 12/2008 |
| WO | 2009033469 A1 | 3/2009 |
| WO | 2009042196 A2 | 4/2009 |
| WO | 2009053497 A1 | 4/2009 |
| WO | 2009061389 A2 | 5/2009 |
| WO | 2009094188 A2 | 7/2009 |
| WO | 2009116041 A2 | 9/2009 |
| WO | 2009149462 A2 | 12/2009 |
| WO | 2010011699 A2 | 1/2010 |
| WO | 2010121076 A2 | 10/2010 |
| WO | 2013106585 A1 | 7/2013 |
| WO | 2015085218 A1 | 6/2015 |
| WO | 2018222799 A1 | 12/2018 |

OTHER PUBLICATIONS

H.R. Andersen "History of Percutaneous Aortic Valve Prosthesis," Herz No. 34. pp. 343-346. 2009.

Pavcnik, et al. "Development and initial Experimental Evaluation of a Prosthetic Aortic Valve for Transcatheter Placement," Cardiovascular Radiology, vol. 183, No. 1. pp. 151-154. 1992.

Bailey, S. "Percutaneous Expandable Prosthetic Valves," Textbook of Interventional Cardiology vol. 2, 2nd Ed. pp. 1268-1276. 1994.

Al-Khaja, et al. "Eleven Years' Experience with Carpentier-Edwards Biological Valves in Relation to Survival and Complications," European Journal of Cardiothoracic Surgery, vol. 3. pp. 305-311. 1989.

Ross, "Aortic Valve Surgery," At a meeting of the Council on Aug. 4, 1966. pp. 192-197.

Sabbah, et al. "Mechanical Factors in the Degeneration of Porcine Bioprosthetic Valves: An Overview," Journal of Cardiac Surgery, vol. 4, No. 4. pp. 302-309. 1989.

Wheatley, "Valve Prostheses," Operative Surgery, 4th ed. pp. 415-424. 1986.

Uchida, "Modifications of Gianturco Expandable Wire Stents," American Journal of Roentgenology, vol. 150. pp. 1185-1187. 1986.

Walther T, Dehdashtian MM, Khanna R, Young E, Goldbrunner PJ, Lee W. Trans-catheter valve-in-valve implantation: in vitro hydrodynamic performance of the SAPIEN+cloth trans-catheter heart valve in the Carpentier-Edwards Perimount valves. Eur J Cardiothorac Surg. 2011;40(5):1120-6. Epub Apr. 7, 2011.

Fontaine, M.D., Arthur B., et al., "Vascular Stent Prototype; Results of Preclinical Evaluation", p. 29-34; Technical Developments and Instrumentation; Jan.-Feb. 1996, vol. 7, No. 1.

Fontaine, M.D., Arthur B., et al., "Prototype Stent: Invivo Swine Studies in the Biliary System1", p. 101-105, Journal of Vascular and Interventional Radiology; Jan.-Feb. 1997; vol. 8, No. 1.

Patrick W. Serruys, Nicolo Piazza, Alain Cribier, John Webb, Jean-Claude Laborde, Peter de Jaegere, "Transcatheter Aortic Valve Implantation: Tips and Tricks to Avoid Failure"; we file the table of contents and pp. 18 to 39 (Chapter 2) and pp. 102-114 (Chapter 8); the publication date according to the "Library of Congress Cataloging-in-Publication Data" is Nov. 24, 2009.

* cited by examiner

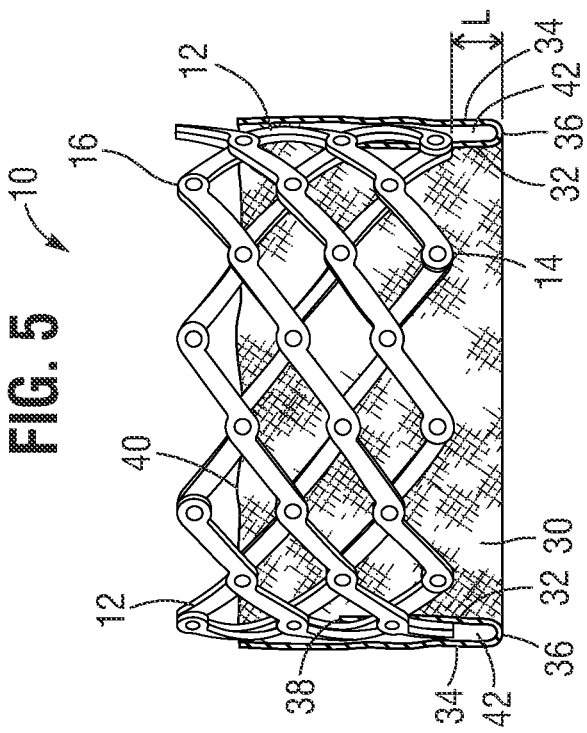
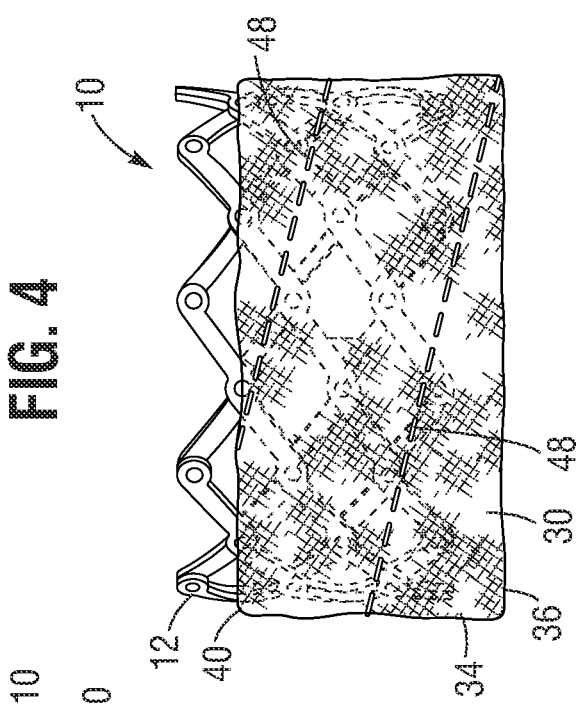
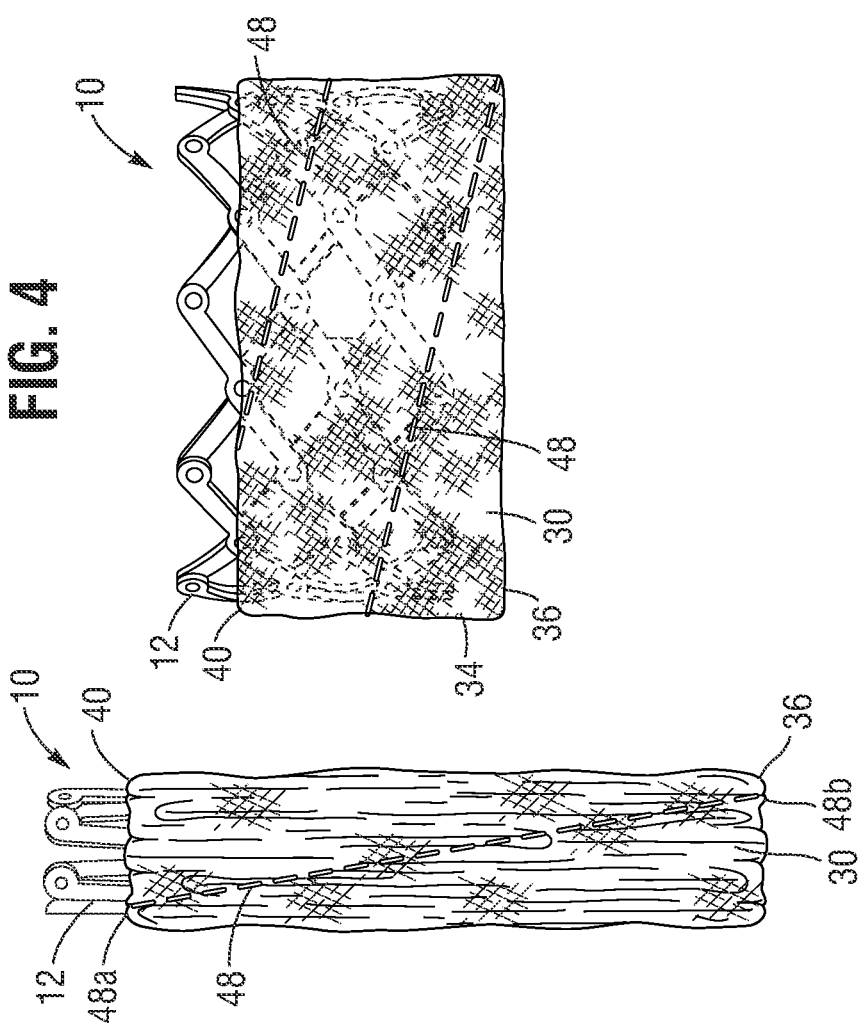

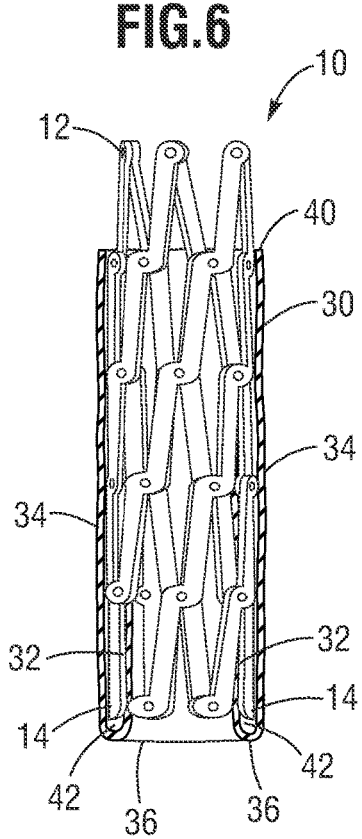
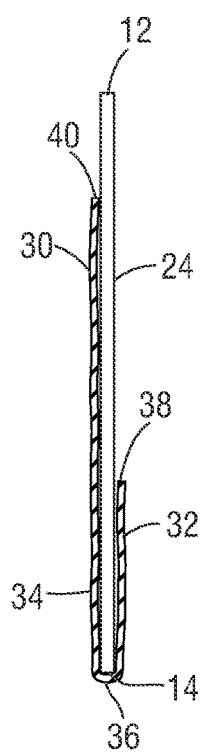
FIG. 6
FIG. 7
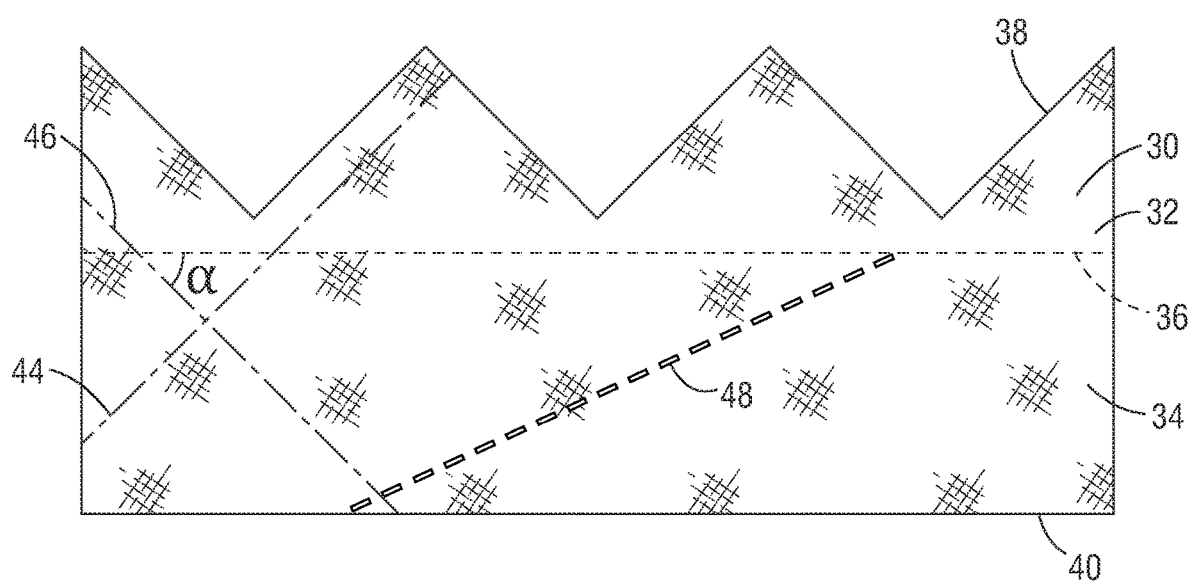
FIG. 8

PROSTHETIC VALVE

CROSS-REFERENCE TO RELATED APPLICATIONS

This application is a continuation of PCT Patent Application No. PCT/US2020/014701, filed Jan. 23, 2020, which claims the benefit of U.S. Provisional Application No. 62/797,837, filed Jan. 28, 2019, both of which applications are incorporated herein by reference.

FIELD

The present disclosure concerns embodiments of a prosthetic valve for implantation into body ducts, such as native heart valve annuluses, and methods of implanting the prosthetic valve.

BACKGROUND

The human heart can suffer from various valvular diseases. These valvular diseases can result in significant malfunctioning of the heart and ultimately require replacement of the native valve with an artificial valve. There are a number of known artificial valves and a number of known methods of implanting these artificial valves in humans. Because of the drawbacks associated with conventional open-heart surgery, percutaneous and minimally-invasive surgical approaches are garnering intense attention. In one technique, a prosthetic heart valve is configured to be implanted in a much less invasive procedure by way of catheterization. For example, a prosthetic heart valve can be mounted in a crimped state on the distal end of a delivery device and advanced through the patient's vasculature (e.g., through a femoral artery and the aorta) until the prosthetic valve reaches the implantation site in the heart. The prosthetic valve is then expanded to its functional size, for example, by inflating a balloon on which the prosthetic valve is mounted, or by deploying the prosthetic valve from a sheath of the delivery device so that the prosthetic valve can self-expand to its functional size, or by other means. Despite the recent advancements in percutaneous valve technology, there remains a need for improved prosthetic valves and methods for delivery of such valves.

Known prosthetic valves can be radially compressible and expandable between a radially compressed state and a radially expanded state. Thus, the prosthetic valves can be crimped on an implant delivery apparatus in the radially compressed state during delivery, and then expanded to the radially expanded state once the prosthetic valve reaches the implantation site.

A prosthetic valve typically includes a frame with a valvular structure (e.g., leaflets) mounted therein, an inner skirt secured to the inside of the frame, and optionally, an outer skirt secured to the exterior of the frame. The inner skirt can serve several functions. For example, the inner skirt can function as a sealing member to prevent (or decrease) paravalvular leakage and to anchor the leaflets to the frame. The outer skirt can cooperate with the inner skirt to further reduce or avoid paravalvular leakage after implantation of the valve. The inner and outer skirts can be secured to the frame by suturing or stitching the fabric of the respective skirts to the frame.

The inner skirt desirably comprises a tough, tear resistant material such as polyethylene terephthalate (PET), although various other synthetic or natural materials can be used. Skirts formed from conventional woven PET or similar fabrics are substantially non-elastic, and thus can hardly be stretched. The lack of skirt elasticity can create a challenge for crimping the prosthetic valve. For example, crimping the prosthetic valve tends to reduce the frame's diameter while elongating the frame in the axial direction. Because the skirt is usually sutured to the frame, the inelasticity of the skirt can constrain the axial elongation of the frame. In some circumstances, crimping can create substantial stress of the fabric at the suture points such that it may lead to suture tears, fabric tear, or frame distortion. Further, depending on how the skirt is sutured to the frame, constraint of the skirt during crimping can be localized such that some areas of the skirt may conform to the frame more tightly than other areas. Such non-uniform tightening can lead to undesired uneven attachment of the skirt to the frame, and can further cause tearing of sutures and/or the fabric, or distortion of the frame. One possible solution to this problem is to size the skirt such that there is slack in the radial direction when the prosthetic valve is in the radially expanded state. The slack permits axial elongation of the prosthetic valve during the crimping process without being restricted or constrained by the skirt. However, the use of extra fabric can increase the radial profile of the prosthetic valve, which is disadvantageous for transcatheter valve implantation. Additionally, the loose fabric can protrude through the cells of the frame and contact the leaflets, causing undesirable abrasion of the leaflets. Accordingly, improvements to skirts for prosthetic valves are desirable.

SUMMARY

Described herein are examples of prosthetic valves and related methods of implanting the prosthetic valves. Prosthetic valves disclosed herein can be implanted within any of the native valves of the heart (the aortic, mitral, tricuspid and pulmonary valves). In some embodiments, the prosthetic valve can be delivered through the vasculature and implanted to the heart of a patient by using a delivery apparatus.

Certain embodiments of the disclosure concern a prosthetic valve having an annular frame, a valvular structure, and an annular skirt. The annular frame can be radially expandable and compressible between a radially compressed configuration and a radially expanded configuration. The valvular structure can be positioned within the frame and configured to permit the flow of blood through the prosthetic valve in one direction and block the flow of blood in an opposing direction. The annular skirt can have an outer portion covering at least a portion of an outer surface of the frame and an inner portion covering at least a portion of an inner surface of the frame. The skirt can be folded around an inflow end of the frame so as to define a fold between the inner portion and outer portion. The skirt can be sized such that when the frame is in the expanded configuration, the outer portion of the skirt conforms to the outer surface of the frame and the inflow end of the frame is axially spaced from the fold to form an axially extending gap between the frame and the fold, and when the frame is radially compressed from the expanded configuration to the compressed configuration, the inflow end of the frame moves axially within the gap closer to the fold.

In some embodiments, the outer portion of the skirt can be secured to a row of struts defining an outflow end of the frame.

In some embodiments, the outer portion of the skirt can be stretched in a circumferential direction when the frame is in the expanded configuration.

In some embodiments, the skirt can comprise a non-elastic fabric.

In some embodiments, the fabric can be woven using polyethylene terephthalate fibers in both warp and weft directions.

In some embodiments, the skirt can be woven from a first set of fibers oriented in a first direction and a second set of fibers oriented in a second direction, neither the first nor the second direction being perpendicular to the fold.

In some embodiments, the first direction can be generally perpendicular to the second direction. The second direction can form an angle about 45 degrees relative to the fold.

In some embodiments, the valvular structure can include a plurality of leaflets, each leaflet having an inflow edge portion. The inflow edge portions of the leaflets can define an undulating shape.

In some embodiments, the inner portion of the skirt can have an undulating outflow edge sutured to the inflow edge portions of the leaflets.

In some embodiments, the prosthetic valve can include a tether coupled to the skirt. The tether can be configured to prevent the fold from moving inside the frame when the frame is radially expanded from the compressed configuration to the expanded configuration.

Certain embodiments of the disclosure also concern a prosthetic valve having an annular frame, a valvular structure, and an annular skirt. The annular frame can have an inflow end and an outflow end, and the frame can be radially expandable and compressible between a radially compressed configuration and a radially expanded configuration. The valvular structure can be positioned within the frame and configured to permit the flow of blood through the prosthetic valve in one direction and block the flow of blood in an opposing direction. The annular skirt can have a fold extending around the inflow end of the frame so as to cover at least a portion of an outer surface of the frame and at least a portion of an inner surface of the frame. When the frame is in the radially expanded configuration, an outer portion of the skirt can tightly conform to the outer surface of the frame and the inflow end of the frame can be axially spaced from the fold to form an axially extending gap between the frame and the fold. When the frame is in the radially compressed configuration, the inflow end of the frame can extend axially so as to at least partially fill the axially extending gap.

In certain embodiments, the valvular structure can include a plurality of leaflets, each leaflet having an inflow edge portion, and the inflow edge portions of the leaflets can define an undulating, curved scalloped shape that follows a plurality of interconnected strut segments of the frame along a circumferential direction when the frame is in the radially expanded configuration.

In certain embodiments, the outer portion of the skirt can be axially longer than the inner portion of the skirt.

In certain embodiments, the outer portion of the skirt can be stretched in a circumferential direction when the frame is in the expanded configuration.

In certain embodiments, the prosthetic valve can include a tether coupled to the skirt and extending at an oblique angle relative to a longitudinal axis of the frame such that the tether can apply a tension to the skirt so as to prevent the fold from moving inside the frame when the frame is radially expanded from the compressed configuration to the expanded configuration.

Also disclosed herein are methods of implanting a prosthetic valve mounted on a delivery apparatus. The method can include delivering the prosthetic valve in a radially compressed configuration to a target location, the prosthetic valve including an annular frame and an annular skirt having a fold around an inflow end of the frame so as to cover at least a portion of an outer surface of the frame and at least a portion of an inner surface of the frame. The method further includes expanding the prosthetic valve to a radially expanded configuration such that an outer portion of the skirt tightly conforms to the outer surface of the frame, and the inflow end of the frame moves axially away from the fold, thereby forming an axially extending gap between the frame and the fold.

In certain embodiments, the prosthetic valve can further include a valvular structure. The valvular structure can include a plurality of leaflets, each leaflet having an inflow edge portion, and the inflow edge portions of the leaflets can define an undulating, curved scalloped shape that follows a plurality of interconnected strut segments of the frame along a circumferential direction when the frame is in the radially expanded configuration.

In certain embodiments, the outer portion of the skirt can be stretched in a circumferential direction when the frame is in the expanded configuration.

In certain embodiments, when the frame is in the radially compressed configuration, the inflow end of the frame can extend axially all the way to the fold so as to completely fill the axially extending gap.

In certain embodiments, the prosthetic valve can include a tether coupled to the skirt. The tether can be configured to prevent the fold from moving inside the frame when the frame is radially expanded from the compressed configuration to the expanded configuration.

Further disclosed herein are embodiments of a prosthetic valve including an annular frame and an annular skirt covering at least a portion of an outer surface of the frame. The annular frame can have an inflow end and an outflow end, and the frame can be radially expandable and compressible between a radially compressed configuration and a radially expanded configuration. The lower edge of the skirt can extend over the inflow end of the frame. The skirt can be attached to the frame by a plurality of sutures. The sutures can be positioned on a plurality of selected struts of the frame such that the sutures form undulating, scallop-shaped suture lines. Each of the suture lines can form an about 45-degree angle relative to a longitudinal axis of the frame when the frame is in the radially expanded configuration. The skirt can be woven from a first set of non-elastic fibers oriented in a first direction and a second set of non-elastic fibers oriented in a second direction. The first direction can be generally perpendicular to the second direction which can form an angle about 45 degrees relative to the lower edge of the skirt. The skirt can be sized such it tightly conforms to the outer surface of the frame without any slack when the frame is in the radially expanded configuration.

In some embodiments, the skirt can fold around the inflow end of the frame so that the lower edge of the skirt defines a fold. When the frame is in the radially expanded configuration, the inflow end of the frame can be axially spaced from the fold to form an axially extending gap between the frame and the fold. When the frame is radially compressed from the expanded configuration to the compressed configuration, the inflow end of the frame can move axially within the gap closer to the fold.

In some embodiments, when the frame is radially compressed, the skirt can billow out to form folded flaps between the scallop-shaped suture lines.

In some embodiments, each flap can be folded over its adjacent flap in a circumferential direction so as to maintain a low crimping profile of the prosthetic valve.

Certain embodiments of the disclosure concern a prosthetic valve that includes an annular frame having an inflow end and an outflow end, at least one actuator mounted to the frame, and an annular skirt having a fold extending around the inflow end of the frame so as to cover at least a portion of an outer surface of the frame and at least a portion of an inner surface of the frame. The actuator can be configured to radially expand or compress the frame between a radially compressed configuration and a radially expanded configuration. When the frame is in the radially expanded configuration, an outer portion of the skirt can tightly conform to the outer surface of the frame and the inflow end of the frame can be axially spaced from the fold to form an axially extending gap between the frame and the fold. When the frame is in the radially compressed configuration, the inflow end of the frame can extend axially so as to at least partially fill the axially extending gap.

In some embodiments, the at least one actuator can be one of a plurality of actuators mounted to and equally spaced around the inner surface of the frame.

In some embodiments, the at least one actuator can include a first anchor attached to a first location of the frame, a second anchor secured to a second location of the frame, and a rod extending through the first anchor and the second anchor. The second location can be closer to the inflow end of the frame than the first location. The rod can be configured to increase or decrease a distance between the first and second locations so as to radially compress or radially expand the frame, respectively.

In some embodiments, the rod can include external threads that are configured to matingly engage with internal threads of the second anchor.

In some embodiments, the first location can be a junction between two overlaying struts of the frame, and the first anchor can be hingedly connected to the junction by a fastener.

In some embodiments, the at least one actuator can include a rod received at least partially within a sleeve, and the axial movement of the rod relative to the sleeve can cause radial expansion or compression of the frame.

In some embodiments, the at least one actuator can include a locking mechanism configured to lock the frame in the radially expanded configuration.

In some embodiments, the at least one actuator can include an attachment member that is configured to form a releasable connection with a corresponding actuation member of a delivery apparatus such that the actuation member of the delivery apparatus can apply force to the at least one actuator for radially compressing or expanding the frame.

In some embodiments, the prosthetic valve can further include a valvular structure positioned within the frame and configured to permit the flow of blood through the prosthetic valve in one direction and block the flow of blood in an opposing direction.

In some embodiments, the valvular structure can include a plurality of leaflets, each leaflet having an inflow edge portion, and the inflow edge portions of the leaflets can define an undulating, curved scalloped shape that follows a plurality of interconnected strut segments of the frame along a circumferential direction when the frame is in the radially expanded configuration.

In some embodiments, the outer portion of the skirt can be axially longer than the inner portion of the skirt.

In some embodiments, the outer portion of the skirt can have about the same axial length as the inner portion of the skirt.

In some embodiments, the outer portion of the skirt can be axially shorter than the inner portion of the skirt.

In some embodiments, the outer portion of the skirt can be stretched in a circumferential direction when the frame is in the expanded configuration.

In some embodiments, an upper edge of the outer portion of the skirt can be generally straight before being attached to the frame.

In some embodiments, the upper edge of the outer portion of the skirt can be attached to the frame at a plurality of pivot joints formed by overlapping struts of the frame.

In some embodiments, an upper edge of the outer portion of the skirt can have an undulating shape and is sutured along a row of strut segments of the frame.

In some embodiments, the prosthetic valve can further include a tether coupled to the skirt and extending at an oblique angle relative to the fold such that the tether applies a tension to the skirt so as to prevent the fold from moving inside the frame when the frame is radially expanded from the compressed configuration to the expanded configuration.

In some embodiments, the oblique angle can range from about 10° to about 80°. In some embodiments, the oblique angle can range from about 30° to about 60°. In some embodiments, the oblique angle can be about 45°.

In some embodiments, a first end of the tether can be located at an outflow edge portion of the outer portion of the skirt, and a second end of the tether can be located adjacent the fold.

In some embodiments, the tether can include a suture that is stitched to the outer portion of the skirt using in-and-out stitches.

In some embodiments, the tether can include an elastic material.

In some embodiments, the tether can be one of a plurality of tethers, each of which can form an oblique angle relative to the fold.

Certain embodiments of the disclosure also concern a prosthetic valve that includes an annular frame being radially expandable and compressible between a radially compressed configuration and a radially expanded configuration, an annular skirt having an outer portion covering at least a portion of an outer surface of the frame and an inner portion covering at least a portion of an inner surface of the frame, and a tether coupled to the skirt to prevent the fold from moving inside the frame when the frame is radially expanded from the compressed configuration to the expanded configuration. The skirt can be folded around an inflow end of the frame so as to define a fold between the inner portion and outer portion. The skirt can be sized such that when the frame is in the expanded configuration, the outer portion of the skirt can conform to the outer surface of the frame and the inflow end of the frame can be axially spaced from the fold to form an axially extending gap between the frame and the fold, and when the frame is radially compressed from the expanded configuration to the compressed configuration, the inflow end of the frame can move axially within the gap closer to the fold.

In some embodiments, the prosthetic valve can further include a valvular structure positioned within the frame and configured to permit the flow of blood through the prosthetic valve in one direction and block the flow of blood in an opposing direction.

In some embodiments, the valvular structure can include a plurality of leaflets, each leaflet having an inflow edge portion, and the inflow edge portions of the leaflets can define an undulating shape.

In some embodiments, the inner portion of the skirt can have an undulating outflow edge sutured to the inflow edge portions of the leaflets.

In some embodiments, the outer portion of the skirt can be secured to a row of struts defining an outflow end of the frame.

In some embodiments, the outer portion of the skirt can be stretched in a circumferential direction when the frame is in the expanded configuration.

In some embodiments, the skirt can include a non-elastic fabric.

In some embodiments, the fabric can include polyethylene terephthalate fibers.

In some embodiments, the polyethylene terephthalate fibers can have a thickness of about 20-denier.

In some embodiments, the polyethylene terephthalate fibers can have an inter-fiber spacing ranging from about 155 fibers per inch to about 180 fibers per inch. In some embodiments, the polyethylene terephthalate fibers can have an inter-fiber spacing about 160 fibers per inch.

In some embodiments, the skirt can be woven from a first set of fibers oriented in a first direction and a second set of fibers oriented in a second direction, neither the first nor the second direction being perpendicular to the fold.

In some embodiments, the first direction can be generally perpendicular to the second direction which forms an angle about 45 degrees relative to the fold.

In some embodiments, the first set of fibers can extend generally parallel to a first set of struts of the frame and the second set of fibers can extend generally parallel to a second set of struts of the frame when the frame is in the expanded configuration, and the second set of struts can overlap the first set of struts to form junctions of the frame.

In some embodiments, the tether can extend at an oblique angle relative to the fold and the tether can be configured to apply a tension to the skirt when the frame is in the expanded configuration.

In some embodiments, the oblique angle can be about 45°.

In some embodiments, a first end of the tether can be located at an outflow edge portion of the outer portion of the skirt, and a second end of the tether can be located adjacent the fold.

In some embodiments, the tether can include a suture that is stitched to the outer portion of the skirt using in-and-out stitches.

In some embodiments, the tether can include an elastic material.

Certain embodiments of the disclosure also concern a prosthetic valve that includes an annular frame being radially expandable and compressible between a radially compressed configuration and a radially expanded configuration, and an annular outer skirt covering at least a portion of an outer surface of the frame. When the frame is in the radially compressed configuration, portions of the outer skirt can billow out to form longitudinally extending folded flaps.

In some embodiments, each flap can be further folded in a circumferential direction so as to maintain a low crimping profile of the prosthetic valve.

In some embodiments, each flap can at least partially overlap an adjacent flap in the circumferential direction.

In some embodiments, the outer skirt can be connected to struts of the frame along a zig-zag shaped attachment line.

In some embodiments, the outer skirt can be connected to the struts of the frame with sutures along the zig-zag shaped attachment line.

In some embodiments, the outer skirt can be not connected to any struts of the frame or other components of the prosthetic valve at locations not along the zig-zag shaped attachment line.

In some embodiments, the outer skirt can be connected to the frame only along the zig-zag shaped attachment line.

In some embodiments, the prosthetic valve can further include a plurality of leaflets, each leaflet having an inflow edge portion attached to the struts of the frame along the zig-zag shaped attachment line.

In some embodiments, the flaps can be V-shaped.

In some embodiments, the prosthetic valve can further include an annular inner skirt covering at least a portion of an inner surface of the frame, and the outer skirt can be connected to the inner skirt via a fold extending around an inflow end of the frame.

In some embodiments, when the frame is in the radially expanded configuration, the outer skirt can be configured to tightly conform to the outer surface of the frame and the inflow end of the frame can be axially spaced from the fold to form an axially extending gap between the frame and the fold, and when the frame is in the radially compressed configuration, the inflow end of the frame can be configured to extend axially so as to at least partially fill the axially extending gap.

In some embodiments, an axial length of the gap can range from about 4 mm to about 8 mm when the frame is in the radially expanded configuration. In some embodiments, the axial length of the gap can be about 6 mm when the frame is in the radially expanded configuration.

In some embodiments, the inflow end of the frame can extend axially to and completely fill the gap when the frame is in the radially compressed configuration.

In some embodiments, the inner skirt can fold inwardly toward an interior of the frame when the frame is in the radially compressed configuration.

In some embodiments, the prosthetic valve can further include a tether coupled to the outer skirt and extending at an oblique angle relative to the fold such that the tether applies a tension to the outer skirt so as to prevent the fold from moving inside the frame when the frame is radially expanded from the compressed configuration to the expanded configuration.

In some embodiments, the tether can include a suture that is stitched to the outer skirt using in-and-out stitches.

In some embodiments, the tether can include an elastic material.

Certain embodiments of the disclosure further concern a method of assembling a prosthetic valve. The method can include receiving an annular frame that is radially expandable and compressible between a radially compressed configuration and a radially expanded configuration, and attaching an annular skirt to the frame such that the skirt has an outer portion covering at least a portion of an outer surface of the frame and an inner portion covering at least a portion of an inner surface of the frame. The skirt can be folded around an inflow end of the frame so as to define a fold between the inner portion and outer portion. The skirt can be sized such that when the frame is in the expanded configuration, the outer portion of the skirt can conform to the outer surface of the frame and the inflow end of the frame can be axially spaced from the fold to form an axially extending gap between the frame and the fold, and when the frame is radially compressed from the expanded configuration to the compressed configuration, the inflow end of the frame can move axially within the gap closer to the fold.

In some embodiments, attaching the annular skirt to the frame can include suturing an upper edge of the inner portion of the skirt to a selected row of strut segments of the frame from inside the frame.

In some embodiments, attaching the annular skirt to the frame can include suturing the outer portion of the skirt to a row of struts defining an outflow end of the frame.

In some embodiments, the method can further include attaching a valvular structure to the frame. The valvular structure can be configured to permit the flow of blood through the prosthetic valve in one direction and block the flow of blood in an opposing direction.

In some embodiments, the valvular structure can include a plurality of leaflets, each leaflet having an inflow edge portion. The inflow edge portions of the leaflets can define an undulating shape. Attaching the valvular structure to the frame can include suturing the inflow edge portions of the leaflets from inside the frame to a row of interconnected strut segments of the frame along a circumferential direction.

In some embodiments, the method can further include coupling a tether to the skirt in an oblique angle relative to the fold so as to prevent the fold from moving inside the frame when the frame is radially expanded from the compressed configuration to the expanded configuration.

Certain embodiments of the disclosure further concern a method including receiving a prosthetic valve comprising an annular frame that is radially expandable and compressible between a radially compressed configuration and a radially expanded configuration and an annular skirt that covers at least a portion of an outer surface of the frame, compressing the frame to the radially compressed configuration so that portions of the skirt billow out to form longitudinally extending folded flaps, and folding the flaps in a circumferential direction.

In some embodiments, the skirt can be sutured to struts of the frame along a zig-zag shaped attachment line.

In some embodiments, the prosthetic valve can include a plurality of leaflets, and each leaflet can have an inflow edge portion being attached to the struts of the frame along the zig-zag shaped attachment line.

In some embodiments, the skirt can cover at least a portion of an inner surface of the frame and form a fold around an inflow end of the frame.

In some embodiments, the skirt can be sized such that when the frame is in the expanded configuration, the inflow end of the frame can be axially spaced from the fold to form an axially extending gap between the frame and the fold, and when the frame is radially compressed from the expanded configuration to the compressed configuration, the inflow end of the frame can move axially within the gap closer to the fold.

In some embodiments, the prosthetic valve can further include a tether coupled to the skirt at an oblique angle relative to the fold so as to prevent the fold from moving inside the frame when the frame is radially expanded from the compressed configuration to the expanded configuration.

In some embodiments, the method can further include loading the prosthetic valve into a sheath of a delivery apparatus, inserting the prosthetic valve into a patient, advancing the prosthetic valve through the patient's vasculature to an implantation site, and radially expanding the prosthetic valve at the implantation site.

In some embodiments, radially expanding the prosthetic valve can cause the flaps to unfold.

In some embodiments, when the frame is in the radially expanded configuration, the skirt can tightly conform to the outer surface of the frame.

The foregoing and other objects, features, and advantages of the invention will become more apparent from the following detailed description, which proceeds with reference to the accompanying figures.

BRIEF DESCRIPTION OF THE DRAWINGS

FIG. 3 shows a side elevational view of the prosthetic valve depicted in FIG. 1 in a radially compressed configuration, the valve further comprising a skirt attached to the frame.

FIG. 4 shows a side elevational view of the prosthetic valve depicted in FIG. 3 in a radially expanded configuration.

FIG. 5 shows a side cross sectional view of the prosthetic valve when it is fully expanded.

FIG. 6 shows a side cross sectional view of the prosthetic valve when it is partially compressed.

FIG. 7 shows a side cross section of an outermost portion of the prosthetic valve when it is fully compressed.

FIG. 8 shows a flattened view of the skirt.

DETAILED DESCRIPTION

Figure 1:
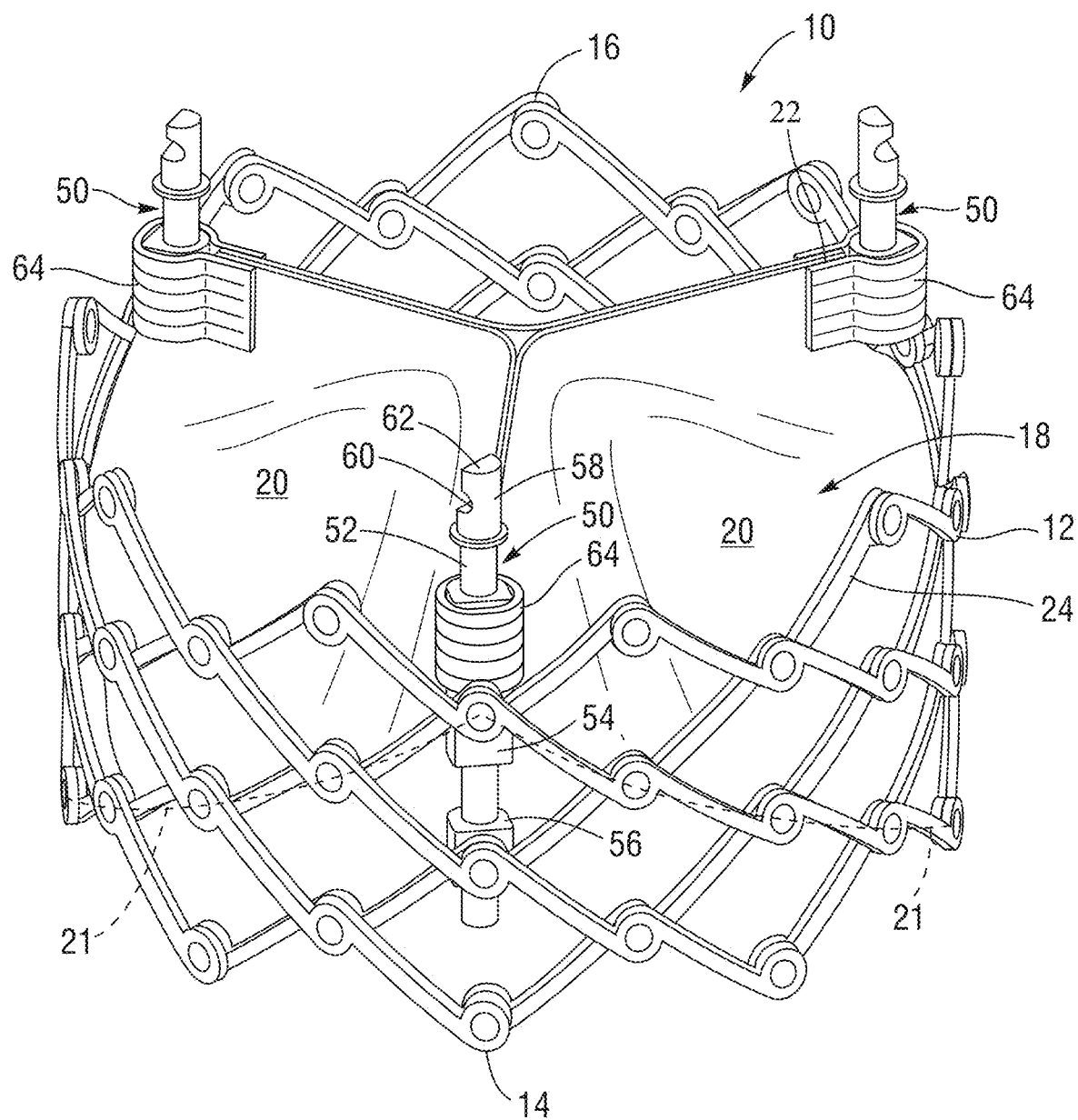
FIG. 1 shows a perspective view of a prosthetic valve, according to one embodiment.

FIG. 1 shows an exemplary prosthetic valve 10, according to one embodiment. In particular embodiments, the prosthetic valve 10 can be implanted within the native aortic annulus, although it also can be implanted at other locations in the heart, including within the native mitral valve, the native pulmonary valve, and the native tricuspid valve. The prosthetic valve 10 can include an annular stent or frame 12 having an inflow end 14 and an outflow end 16. The prosthetic valve 10 can also include a valvular structure 18 which is coupled to and supported inside of the frame 12. The valvular structure 18 is configured to regulate the flow of blood through the prosthetic valve 10 from the inflow end 14 to the outflow end 16.

The prosthetic valve 10 can further include one or more actuators 50 mounted to and equally spaced around the inner surface of the frame 12. Each of the actuators 50 can be configured to form a releasable connection with one or more respective actuators of a delivery apparatus, as further described below.

The valvular structure 18 can include, for example, a leaflet assembly comprising one or more leaflets 20 made of a flexible material. The leaflets 20 can be made from in whole or part, biological material, bio-compatible synthetic materials, or other such materials. Suitable biological material can include, for example, bovine pericardium (or pericardium from other sources). The leaflets 20 can be secured to one another at their adjacent sides to form commissures 22, each of which can be secured to a respective actuator 50 or the frame 12.

In the depicted embodiment, the valvular structure 18 comprises three leaflets 20, which can be arranged to collapse in a tricuspid arrangement. Each leaflet 20 can have an inflow edge portion 21. As shown in FIG. 1, the inflow edge portions 21 of the leaflets 20 can define an undulating, curved scalloped shape that follows or tracks a plurality of interconnected strut segments of the frame 12 in a circumferential direction when the frame 12 is in the radially expanded configuration. The inflow edges of the leaflets can be referred to as a "scallop line." In some embodiments, the inflow edge portions 21 of the leaflets 20 can be sutured to the struts generally along the scallop line. By forming the leaflets 20 with this scalloped geometry, stresses on the leaflets 20 are reduced, which in turn improves durability of the valve 10. Moreover, by virtue of the scalloped shape, folds and ripples at the belly of each leaflet 20 (the central region of each leaflet), which can cause early calcification in those areas, can be eliminated or at least minimized. The scalloped geometry also reduces the amount of tissue material used to form valvular structure 18, thereby allowing a smaller, more even crimped profile at the inflow end 14 of the valve 10.

Further details regarding transcatheter prosthetic heart valves, including the manner in which the valvular structure can be coupled to the frame 12 of the prosthetic valve 10, can be found, for example, in U.S. Pat. Nos. 6,730,118, 7,393,360, 7,510,575, 7,993,394 and 8,652,202, and U.S. patent application Ser. No. 15/978,459, all of which are incorporated herein by reference in their entireties.

Figure 2C:
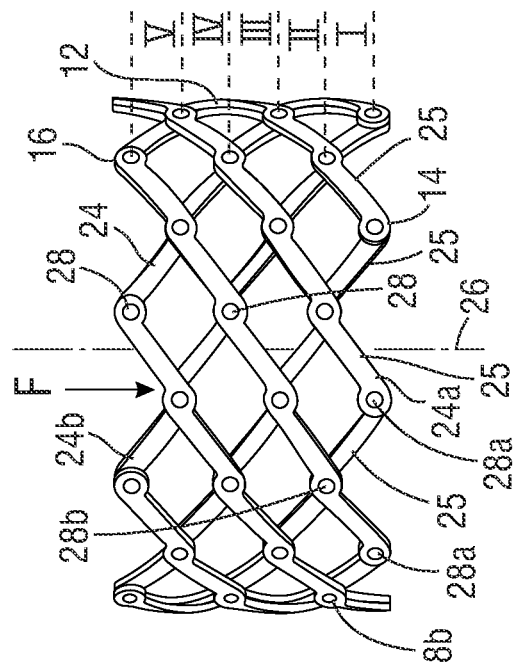
FIG. 2C shows the frame of the prosthetic valve of FIG. 1 shown in a fully radially expanded configuration.
Figure 2B:
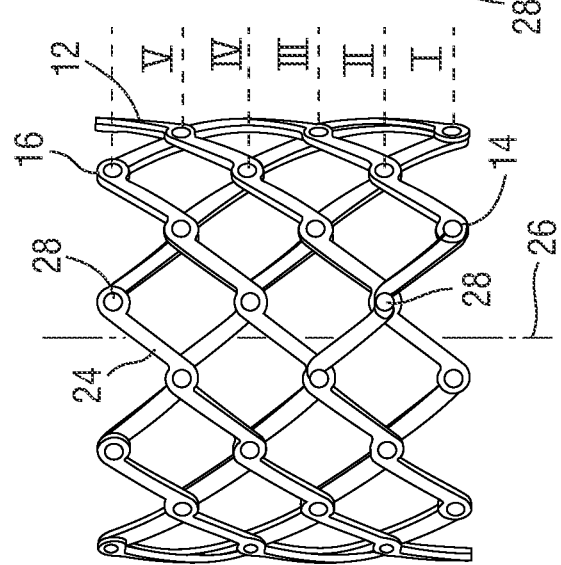
FIG. 2B shows the frame of the prosthetic valve of FIG. 1 shown in a partially radially expanded configuration.
Figure 2A:
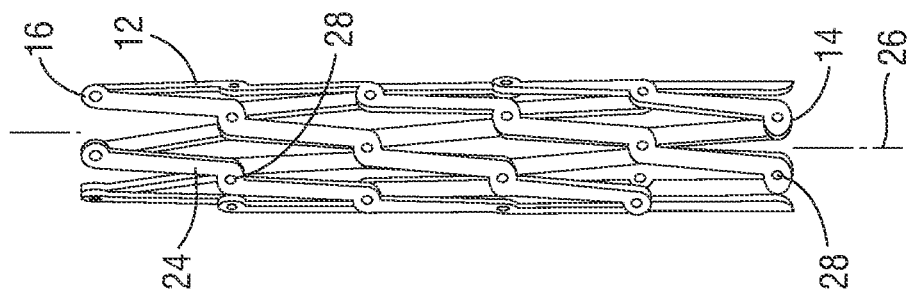
FIG. 2A shows the frame of the prosthetic valve of FIG. 1 shown in a radially compressed configuration.

The prosthetic valve 10 can be radially compressible and expandable between a radially compressed configuration and a radially expanded configuration. FIGS. 2A-2C show the bare frame 12 of the prosthetic valve 10 (without the leaflets and other components) for purposes of illustrating expansion of the prosthetic valve 10 from the radially compressed configuration to the radially expanded configuration. FIG. 2A shows the frame 12 in the radially compressed configuration, FIG. 2B shows the frame 12 in a partially expanded configuration, and FIG. 2C shows the frame 12 in the fully radially expanded configuration.

In the illustrated embodiment, the prosthetic valve 10 can be mechanically expanded from the radially configuration to the radially expanded configuration. For example, the prosthetic valve 10 can be radially expanded by maintaining the inflow end 14 of the frame 12 at a fixed position while applying a force (F) in the axial direction against the outflow end 16 toward the inflow end 14. Alternatively, the prosthetic valve 10 can be expanded by applying an axial force against the inflow end 14 while maintaining the outflow end 16 at a fixed position, or by applying opposing axial forces to the inflow and outflow ends 14, 16, respectively.

In the illustrated embodiment, expansion and compression forces are applied to the frame by the actuators 50. Referring again to FIG. 1, each of the actuators 50 can comprise a screw or threaded rod 52, a first anchor in the form of a cylinder or sleeve 54, and a second anchor in the form of a threaded nut 56. The rod 52 extends through the sleeve 54 and the nut 56. The sleeve 54 can be secured to the frame 12, such as with a fastener that forms a hinge at the junction between two struts. Each actuator 50 is configured to increase the distance between the attachment locations of a respective sleeve 54 and nut 56, which causes the frame 12 to elongate axially and compress radially, and to decrease the distance between the attachment locations of a respective sleeve 54 and nut 56, which causes the frame 12 to foreshorten axially and expand radially.

For example, each rod 52 can have external threads that engage internal threads of the nut 56 such that rotation of the rod causes corresponding axial movement of the nut 56 toward or away from the sleeve 54 (depending on the direction of rotation of the rod 52). This causes the hinges supporting the sleeve 54 and the nut 56 to move closer towards each other to radially expand the frame or to move farther away from each other to radially compress the frame, depending on the direction of rotation of the rod 52.

In other embodiments, the actuators 50 can be reciprocating type actuators configured to apply axial directed forces to the frame to produce radial expansion and compression of the frame. For example, the rod 52 of each actuator can be fixed axially relative to the sleeve 56 and slidable relative to the sleeve 54. Thus, in this manner, moving the rod 52 distally relative to the sleeve 54 and/or moving the sleeve 54 proximally relative to the rod 52 radially compresses the frame. Conversely, moving the rod 52 proximally relative to the sleeve 54 and/or moving the sleeve 54 distally relative to the rod 52 radially expands the frame.

When reciprocating type actuators are used, the prosthetic valve can also include one or more locking mechanisms that retain the frame in the expanded state. The locking mechanisms can be separate components that are mounted on the frame apart from the actuators, or they can be a subcomponent of the actuators themselves.

Each rod 52 can include an attachment member 58 along a proximal end portion of the rod 52 configured to form a releasable connection with a corresponding actuator of a delivery apparatus. The actuator(s) of the delivery apparatus can apply forces to the rods for radially compressing or expanding the prosthetic valve 10. The attachment member 58 in the illustrated configuration comprises a notch 60 and a projection 62 that can engage a corresponding projection of an actuator of the delivery apparatus.

In the illustrated embodiments, the prosthetic valve 10 includes three such actuators 50, although a greater or fewer number of actuators could be used in other embodiments. The leaflets 20 can have commissure attachments members 64 that wrap around the sleeves 54 of the actuators 50. Further details of the actuators, locking mechanisms and delivery apparatuses for actuating the actuators can be found in U.S. Patent Application Nos. 62/548,855, 62/430,810, Ser. No. 15/831,197 (published as U.S. Publication No. 2018/0153689) and Ser. No. 15/978,459, each of which is incorporated herein by reference in its entirety. Any of the actuators and locking mechanisms disclosed in the previously filed applications can be incorporated in any of the prosthetic valves disclosed herein. Further, any of the delivery apparatuses disclosed in the previously filed applications can be used to deliver and implant any of the prosthetic valves discloses herein.

The frame 12 can be made of any of various suitable materials, such as stainless steel, a cobalt chromium alloy, or a nickel titanium alloy ("NiTi"), for example Nitinol. As shown, the frame 12 can include a plurality of interconnected struts 24 arranged in a lattice-type pattern. The struts 24 are shown as positioned diagonally, or offset at an angle relative to, and radially offset from, a longitudinal axis 26 of the prosthetic valve 10 when the prosthetic valve 10 is in the expanded configuration. In other implementations, the struts 24 can be offset by a different amount than depicted in FIGS. 2B and 2C, or some or all of the struts 24 can be positioned parallel to the longitudinal axis 26 of the prosthetic valve 10.

In the depicted embodiment, the struts 24 are pivotably coupled to one another at one or more pivot joints along the length of each strut. For example, in the illustrated configuration, each of the struts 24 can be formed with apertures at opposing ends of the strut and apertures spaced along the length of the strut. Respective hinges can be formed at the locations where struts 24 overlap each other via fasteners, such as rivets or pins 28 that extend through the apertures. The hinges can allow the struts 24 to pivot relative to one another as the frame 12 is radially expanded or compressed, such as during assembly, preparation, or implantation of the prosthetic valve 10.

In the depicted embodiment, the struts 24 are arranged in five rows (I, II, III, IV and V) from the inflow end 14 to the outflow end 16. Each row is defined by the strut segments extending in a zig-zag pattern between adjacent circumferential rows of hinges 28. For example, the first row I is defined by strut segments 25 extending between a first row of hinges 28a at the inflow end of the frame and an adjacent row of hinges 28b. In other embodiments, segments of the struts 24 can be arranged in a different number of rows.

In some embodiments, the frame 12 can be constructed by forming individual components (e.g., the struts and fasteners of the frame) and then mechanically assembling and connecting the individual components together. In other embodiments, the struts 24 are not coupled to each other with respective hinges but are otherwise pivotable or bendable relative to each other to permit radial expansion and contraction of the frame 12. For example, the frame 12 can be formed (e.g., via laser cutting, electroforming or physical vapor deposition) from a single piece of material (e.g., a metal tube). Further details regarding the construction of the frame and the prosthetic valve are described in U.S. patent application Ser. Nos. 15/831,197; 15/995,528; and 62/548,855, all of which are incorporated herein by reference. Additional examples of expandable prosthetic valves that can be used with the delivery apparatuses disclosed herein are described in U.S. Publication No. 2015/0135506 and 2014/0296962, which are incorporated herein by reference.

In other embodiments (not shown), the frame can be made of any of various suitable plastically-expandable materials (e.g., stainless steel, cobalt-chromium alloys, etc.) or self-expanding materials (e.g., Nitinol) as known in the art. When constructed of a plastically-expandable material, the frame (and thus the valve) can be crimped to a radially compressed configuration on a delivery apparatus and then expanded inside a patient by an inflatable balloon or another suitable expansion mechanism. When constructed of a self-expandable material, the frame (and thus the valve) can be crimped to a radially compressed configuration and restrained in the compressed configuration by insertion into a sheath or equivalent mechanism of a delivery apparatus. Once inside the body, the valve can be advanced from the delivery sheath, which allows the valve to expand to its functional size.

As shown in FIGS. 3-7, the prosthetic valve 10 can further include an annular skirt 30 that is attached to the frame 12. A flattened view of the skirt 30 is shown in FIG. 8.

The skirt 30 in the illustrated embodiment can have an inner portion 32 and an outer portion 34. Specifically, the skirt 30 can extend along an inner surface of the frame 12, around the inflow end 14 of the frame 12, and then along the outer surface of the frame so as to define a fold 36 between the inner portion 32 and outer portion 34. When attached to the frame 12, the inner portion 32 can cover at least a portion of an inner surface of the frame 12, the outer portion 34 can cover at least a portion of an outer surface of the frame 12.

The inner portion 32 of the skirt 30 can function as a sealing member to prevent or decrease paravalvular leakage and to anchor the leaflets 20 to the frame 12. The outer portion 34 of the skirt 30 can function as a sealing member for the prosthetic valve 10 by sealing against the tissue of the native valve annulus and helping to reduce paravalvular leakage past the prosthetic valve 10.

As best shown in FIG. 8, the upper edge 38 of the inner portion 32 (which is the outflow edge of the inner portion in the illustrated embodiment) can have an undulating shape that generally follows the shape of a selected row of strut segments 22 of the frame 12 when the frame 12 is in the expanded configuration. In this manner, the upper edge 38 of inner portion 32 can be tightly secured to the selected row of strut segments 22 with sutures. For example, in some embodiments, the upper edge 38 of the inner portion 32 can be sutured to row II of struts segments. In other embodiments, the upper edge 38 of the inner portion 32 can be sutured to row III of struts segments.

In particular embodiments, the suture(s) used to secure the upper edge 38 extends only around the strut segments that are aligned with the scallop line defined by the leaflets 20 (the line that tracks the inflow edge portions 21 of the leaflets). In some embodiments, the upper edge 38 of the inner portion 32 is "sandwiched" between the frame 12 and the leaflets 20. For example, the inflow edge portions 21 of the leaflets can overlap a portion of the inner surface of the inner portion 32 along the upper edge 38 and the leaflets can be secured to the inner portion 32 with sutures extending through the inner surface of the inner portion 32.

In the depicted embodiment, the upper edge 40 of the outer portion 34 (which is the outflow edge of the outer portion in the illustrated embodiment) is generally straight and can be attached to the frame at the pivot joints just below row V of strut segments (see e.g., FIG. 4). In alternative embodiments (not shown), the upper edge 40 of the outer portion 34 can also have an undulating shape (similar to the upper edge of the inner portion 32) so that it can be sutured along the strut segments of a selected row (e.g., row V of strut segments).

In the depicted embodiment, the outer portion 34 of the skirt 30 is axially longer than the inner portion 32 of the skirt 30, i.e., the upper edge 40 of the outer portion 34 extends closer to the outflow end 16 of the frame than the upper edge 38 of the inner portion 32.

Although not shown, in alternative embodiments, the axial length of the outer portion 34 can be the same as or substantially the same as that of the inner portion 32. Alternatively, the outer portion 34 can be axially shorter than the inner portion 32, i.e., the upper edge 38 of the inner portion 32 can extend closer to the outflow end 16 of the frame than the upper edge 40 of the outer portion 34.

As noted above, to deploy the prosthetic valve 10, the frame 12 is radially expanded to a larger diameter (i.e., the deployment diameter). The deployment diameter can be within a working range of diameters defined between a smallest deployment diameter and a largest deployment diameter. In one exemplary but non-limiting embodiment, the smallest deployment diameter is about 26 mm and the largest deployment diameter is about 29 mm.

In particular embodiments, when the frame 12 is radially expanded (see e.g., FIGS. 4-5), the outer portion 34 of the skirt 30 can be slightly stretched in a circumferential direction. In particular embodiments, the skirt 30 can be sized such that when the frame 12 is expanded to a diameter within the working range, the outer portion 34 of the skirt 30 can be stretched so as to tightly or snugly conform to the outer surface of the frame 12, i.e., no slack is formed in the outer portion 34 around the circumferential periphery of the frame 12.

For example, during assembly of the prosthetic valve 10, the skirt 30 can be sutured to the frame 12 when it is expanded to its smallest deployment diameter. The skirt 30 can be sized such that the outer portion 34 tightly conforms to the outer surface of the frame 12 without any slack in the radial direction when the frame 12 is expanded to its smallest deployment diameter. Such tight conformation of the skirt 30 on the outer surface of the frame 12 can inhibit the skirt 30 from protruding through the frame cells, thus preventing abrasion of the leaflets 20.

When the frame 12 is radially expanded to a larger diameter within the working range of deployment diameters, the outer portion 34 of the skirt 30 can further tighten on the frame 12. Thus, in certain embodiments, it can be ensured that the outer portion 34 does not have any slack in the radial direction when the frame 12 is expanded to any diameter within the working range. In some embodiments, in order to ensure that the outer portion 34 fits tightly around the frame 12 at its smallest deployment diameter, the skirt 30 can be cut to a smaller size and the skirt 30 can be mounted on the frame 12 (at its smallest deployment diameter) with some stretching in the circumferential direction.

In other embodiments, the skirt 30 can be sized to fit snugly around the frame without stretching of the skirt in any direction and without any slack in the radial direction when the frame 12 is expanded to its smallest deployment diameter. When the frame is radially expanded to a larger diameter within the working range, the skirt 30 can stretch slightly and tighten around the frame.

In some embodiments, a prosthetic valve may have only one deployment diameter. In such cases, the skirt 30 can be sized to fit snugly around the frame without stretching of the skirt in any direction and without any slack in the radial direction when the frame 12 is expanded to the deployment diameter. In other embodiments, the skirt 30 can be sized such that it is slightly stretched in the circumferential direction when the frame is expanded to the deployment diameter.

In addition, when the frame 12 is radially expanded, the inflow end 14 of the frame 12 can be axially spaced from the fold 36 to form an axially extending gap 42 between the inflow end 14 of frame 12 and the fold 36 (see e.g., FIG. 5). In some embodiments, the gap 42 can have a length (L) ranging from about 4 mm to about 8 mm. In particular embodiments, the length L of the gap 42 can be about 6 mm.

When the frame 12 is radially compressed during crimping (see e.g., FIGS. 6-7), the inflow end 14 of the frame 12 can move axially within the gap 42 closer to the fold 36. In some embodiments, when the frame 12 is in the fully compressed configuration, the inflow end 14 of the frame 12 can extend all the way to the fold 36 such that the frame 12 completely fills the gap 42. In addition, when the frame 12 is in the radially compressed configuration, the outer portion 34 of the skirt 30 can form longitudinal pleats as illustrated in FIG. 3. Meanwhile, the inner portion 32 of the skirt 30 can fold inwardly toward the interior of the frame 12.

The skirt 30 can be formed from any of various suitable biocompatible materials, including any of various synthetic materials (e.g., PET) or natural tissue (e.g., pericardial tissue). In certain embodiments, the skirt 30 is generally non-elastic. For example, the skirt 30 can be woven using PET fibers or yarns in both the warp (longitudinal) and weft (circumferential) directions using a plain weave design. In particular embodiments, the skirt can be assembled on the frame such that the warp fibers extend in the axial direction of the frame and the weft fibers extend in the circumferential direction of the frame. In alternative embodiments, the skirt can be assembled on the frame such that the weft fibers extend in the axial direction of the frame and the warp fibers extend in the circumferential direction of the frame.

In other embodiments, the skirt 30 can be elongated in both the radial and axial directions to certain degrees even if it is still woven using non-elastic fibers. Such pseudo-elasticity can be achieved, for example, by orienting the fibers at angles relative to the height of the skirt and/or increasing the spacing between fibers. For example, as shown in FIG. 8, the skirt 30 can be woven from a first set of fibers (or yarns or strands) extending in a first direction 44, and a second set of fibers (or yarns or strands) extending in a second direction 46, wherein neither the first direction 44 nor the second direction 46 being perpendicular to the fold 36.

In particular embodiments, the first direction 44 can be generally perpendicular to the second direction 46, and the second direction can extend at an angle $\alpha$ of about 45 degrees (e.g., between 15-75 degrees or between 30-60 degrees) relative to the fold 36. In particular embodiments, the first direction 44 extends parallel or substantially parallel to outer struts 24a and the second direction 46 extends parallel or substantially parallel to inner struts 24b when the frame 12 is in its radially expanded state.

In some embodiments, the spacing between the woven fibers (or yarns or strands) can be increased to facilitate elongation of the skirt 30 in both radial and axial directions. For example, for a PET skirt 30 formed from 20-denier yarn, the yarn density can be about 15% to about 30% less than a conventional PET skirt. In some examples, the yarn spacing of the skirt 30 can be from about 155 yarns per inch to about 180 yarns per inch, such as about 160 yarns per inch, whereas in a conventional PET skirt the yarn spacing can be from about 217 yarns per inch to about 247 yarns per inch.

In some embodiments, the fibers can be oriented so that they are parallel or substantially parallel to the struts and/or increasing the spacing between the fibers can allow the skirt 30 to elongate in the axial and/or circumferential direction by up to about 40%. For example, in some embodiments, rotation of the fibers and/or increasing the spacing between the fibers can allow the skirt 30 to elongate in the circumferential direction from the smallest deployment diameter up to the largest deployment diameter.

Because only the upper edge 40 of the outer portion 34 of the skirt 30 is attached to the frame 12 in the illustrated embodiment, the outer portion 34 of the skirt 30 does not constrain axial elongation of the frame 12 when the frame is radially compressed. Thus, the frame 12 is free to move axially within the axially extending gap 42 toward the fold 36 during crimping. Consequently, relatively low crimping forces are needed to crimp the prosthetic valve 10 and overstretching of the skirt 30 can be avoided.

In some embodiments, a tether 48 can be coupled to the skirt 30 to prevent the fold 36 from moving inside the frame 12 when the frame 12 is radially expanded from the compressed configuration to the expanded configuration.

For example, the skirt 30 can include a tether 48 extending diagonally from a first end 48a to a second end 48b located at or near the fold 36 such that the tether 48 forms an oblique angle relative to the fold 36 (see e.g., FIG. 3). In some embodiments, the angle between the tether 48 and the fold 36 can range from about 10° to about 80°. In some embodiments, the angle between the tether 48 and the fold 36 can range from about 30° to about 60°. In one specific embodiment, the angle between the tether 48 and the fold 36 can be about 45°.

In particular embodiments, the first end 48a can be located at the upper edge 40 of the outer portion 34. In another embodiment, the first 48a can be spaced from the upper edge 40. In alternative embodiments, the first end 48a can be attached to an upper portion of the frame 12. In some embodiments (not shown), more than one tether 48 can be coupled to the skirt 30, with each tether 48 extending at an oblique angle relative to the fold 36.

In some embodiments, the tether 48 can be formed from a suture that is stitched to the outer portion 34 of the skirt using, for example, in-and-out stitches, as depicted in FIGS. 3 and 4. Due to the in-and-out stitches, the length of the suture can be longer than the distance traveled by the suture such that the suture line can be elongated if stretched. In this manner, the suture can function similar to a coil, which returns to its original length after being stretched. In other embodiments, the tether 48 can be formed from an elastic material (e.g., an elastic fabric) that can be stretched longitudinally when tension is applied along its length and then return to its original length when tension is removed.

Thus, when the frame 12 is radially expanded from the compressed configuration to the expanded configuration, the tether 48 can be stretched in the lengthwise direction of the tether due to radial expansion of the outer portion 34 of the skirt. As a result, the tether 48 is relatively taut and can hold the fold 36 in place against hemodynamic forces. Thus, the tether 48 can prevent the fold 36 from moving inside the frame 12 when the frame 12 is in the expanded configuration, which may otherwise obstruct the fluid inflow through the valve 10. When the frame 12 is radially compressed, the tether 48 can return to its original length.

The prosthetic valve 10 described above can be mounted on a delivery apparatus and delivered to a target location within the patient. Various embodiments of the delivery apparatus and methods of delivering the prosthetic valve have been described, e.g., in U.S. Patent Application Publication Nos. 2013/0030519, 2010/0049313, 2009/0281619, 2008/0065011, and 2007/0005131, and U.S. patent application Ser. No. 15/831,197, the disclosures of which are incorporated by reference.

To mount the prosthetic valve 10 on the delivery apparatus, the prosthetic valve 10 can be crimped onto a shaft of the delivery apparatus. During crimping, the diameter of the frame 12 decreases while the axial length of the frame 12 elongates. By using a fabric with angled fibers and/or increased spacing between fibers, the skirt 30 can elongate in the axial direction. Further, because the frame 12 is not constrained by the outer portion 34 of the skirt 30, the frame 12 is free to elongate in the axial direction and the inflow end 14 of the frame 12 can extend into the gap 42 during crimping. As noted above, when the frame 12 is radially compressed, the outer portion 34 of the skirt 30 can form longitudinal pleats and the inner portion 32 of the skirt 30 can fold inwardly.

After being delivered to the target location, the prosthetic valve 10 can be expanded until the diameter of the frame 12 is within its working range. During expansion, the diameter of the frame 12 increases while the axial length of the frame 12 shortens. When the prosthetic valve 10 is in the radially expanded configuration, the outer portion 34 of the skirt 30 in particular embodiments can be stretched circumferentially such that it can tightly conform to the outer surface of the frame 12 without any slack in the radial direction. Meanwhile, the inflow end 14 of the frame 12 can move away from the fold 36 to form an axially extending gap 42 between the frame 12 and the fold 36. In some embodiments, one or more tethers 48 can be coupled to the skirt 30 to prevent the fold 36 from moving inside the frame 12 during valve expansion.

Figure 9:
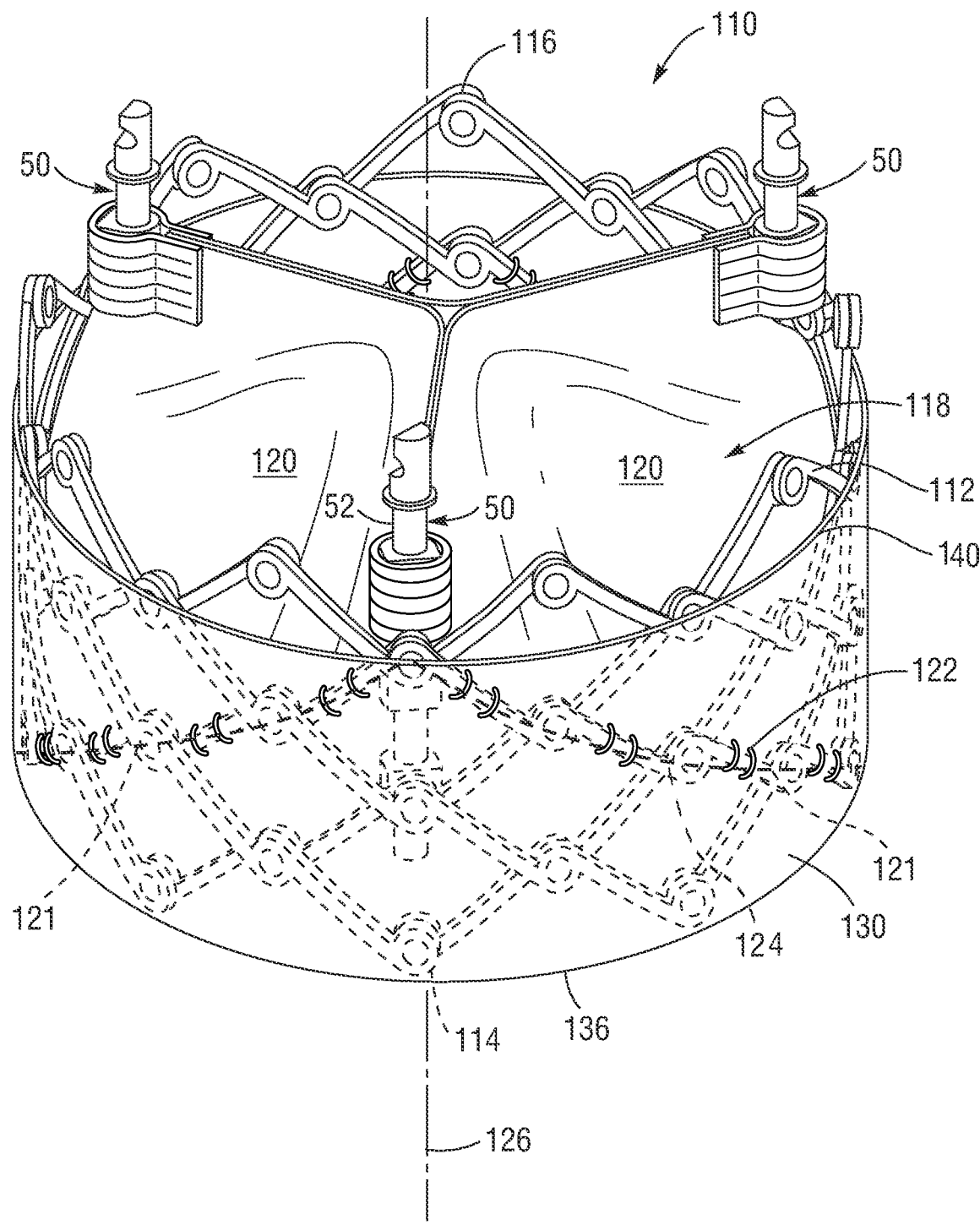
FIG. 9 shows a prospective view of a prosthetic valve, according to an alternative embodiment.

FIG. 9 shows a prosthetic valve 110, according to another embodiment. The prosthetic valve 110 includes a frame 112 that can be radially expandable and compressible between a radially compressed configuration and a radially expanded configuration. Similar to the prosthetic valve 10, the prosthetic valve 110 can include a valvular structure 118 attached to the frame 112, and the valvular structure 118 can include a plurality of leaflets 120 having scalloped geometry (three leaflets are shown in FIG. 9).

The prosthetic valve 110 can further include an outer skirt 130 that covers at least a portion of the outer surface of the frame 112. For example, the lower edge 136 of the skirt 130 (the inflow edge in the illustrated embodiment) can extend from the inflow end 114 of the frame 112, whereas an upper edge 140 of the skirt 130 (the outflow edge in the illustrated embodiment) can be offset from an outflow end 116 of the frame 112. In the depicted embodiment, the frame 112 has five rows of strut segments, and only the row of strut segments defining the outflow end 116 is not covered by the skirt 130. In other embodiments, the skirt 130 can be sized to cover a different portion of the outer surface of the frame than shown in FIG. 9 or it can extend over the entire outer surface of the frame 112. In some embodiments, the skirt 130 can fold around the inflow end 114 of the frame to form a gap similar to the axially extending gap 42 depicted in FIG. 5.

As shown in FIG. 9, the skirt 130 can be sutured to the strut segments 124 of the frame 112 along the scallop line 121 defined by the inflow edges of the leaflets 120. In the illustrated embodiment, the scallop line 121 is a zig-zag shaped attachment line for the skirt 130 and the inflow edges of the leaflets 120. In some embodiments, the sutures 122 can be positioned to wrap around a plurality of struts so that the sutures 122 are positioned along a path that generally follows the scallop line 121. As shown in FIG. 9, each segment of the scallop line 121 (where the inflow edges of the leaflets 120 attach to the frame 112) forms an approximately 45-degree angle relative to the longitudinal axis 126 of the frame 112 when the frame 112 is in the expanded configuration. During crimping of the frame 112, the strut segments along the scallop line 121 move inwardly. Thus, those suture 122 along the scallop lines 121 do not impose stress to the skirt 130. In some embodiments, some of the sutures 122 along the scallop line 121 are configured to be slidable along the struts. Such sliding sutures can further reduce the stress to the skirt 130 when the frame 112 is radially compressed or expanded.

In particular embodiments, the outer skirt 130 is connected to the frame only along the attachment line 121; that is, the outer skirt is not connected to any struts of the frame or other components of the prosthetic valve at locations not along the attachment line 121.

In some embodiments, the outer skirt 130 is connected to the struts of the frame along the attachment line 121, while the inflow edge portions of the leaflets 120 need not be connected to the frame along the attachment line 121.

Figure 10:
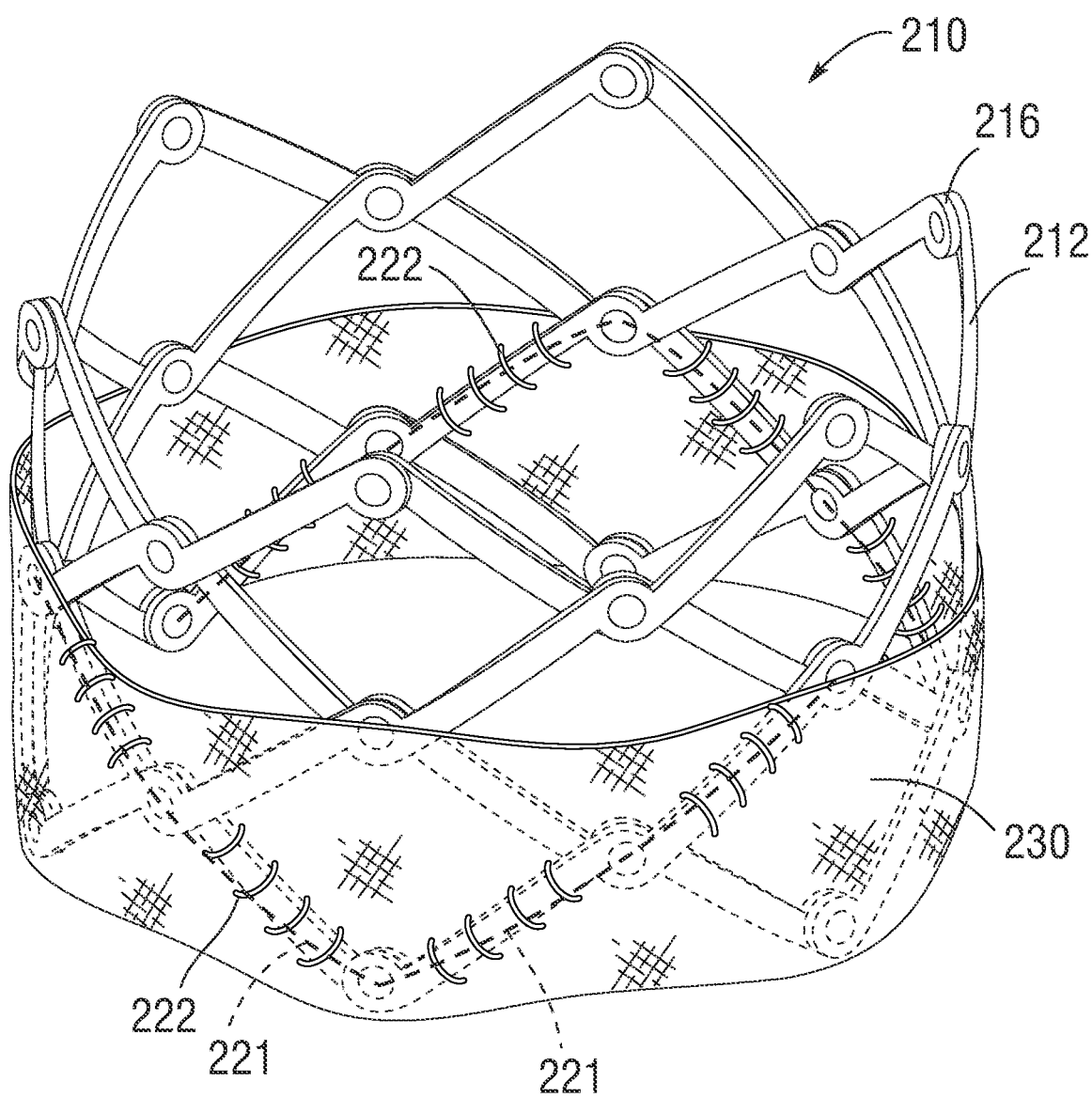
FIG. 10 shows a prospective view of a radially expanded frame of a prosthetic valve, according to another embodiment.

FIG. 10 shows a prosthetic valve 210, according to another embodiment. Similar to the valve 110 discussed above, the valve 210 includes a radially compressible and expandable frame 212 and an outer skirt 230 covering at least a portion of the outer surface of the frame 212. Like valve 110, the skirt 230 can be secured to the frame 212 with sutures 222 along a predefined scallop line 221 (which is a zig-zag shaped attachment line for the skirt in the illustrated embodiment). The valvular structure is not shown in FIG. 10 so that the suture lines 221 in the back of the frame 212 can be clearly seen. The frame 212 in the illustrated embodiment has four rows of strut segments, and the two rows of strut segments closest to near the outflow end 216 are not covered by the skirt 230.

Similar to the skirt 30 discussed above, the fabric of skirt 130 or 230 can be woven using non-elastic fibers that are rotated (e.g., 45 degrees), and optionally with increased spacing between fibers, so that the skirt 130 or 230 can accommodate certain degree of elongation in both radial and axial directions. Likewise, the skirt 130 or 230 can be sized such it tightly conforms to the outer surface of the respective frame 112 or 212 without any slack when the respective frame 112 or 212 is expanded to its smallest working diameter.

Figure 12A:
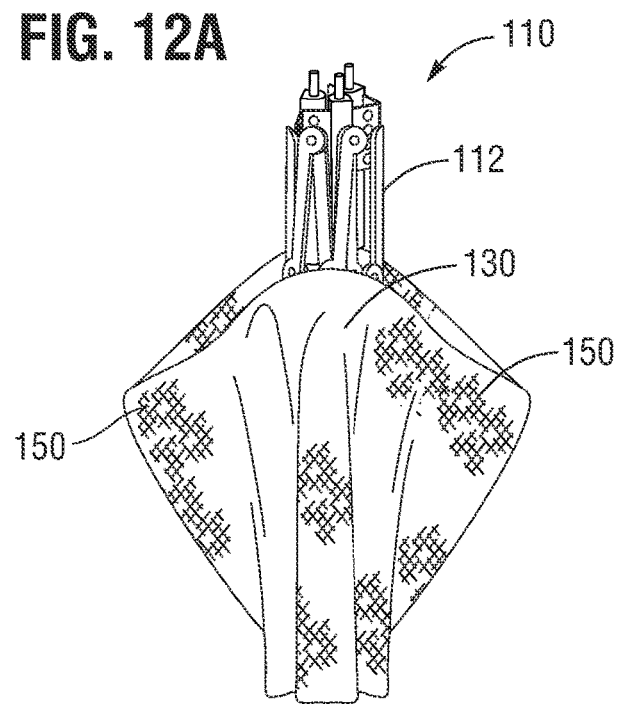
FIG. 12A shows the prosthetic valve of FIG. 9 being fully compressed and the outer portion of the skirt billows out to form folded flaps.
Figure 12B:
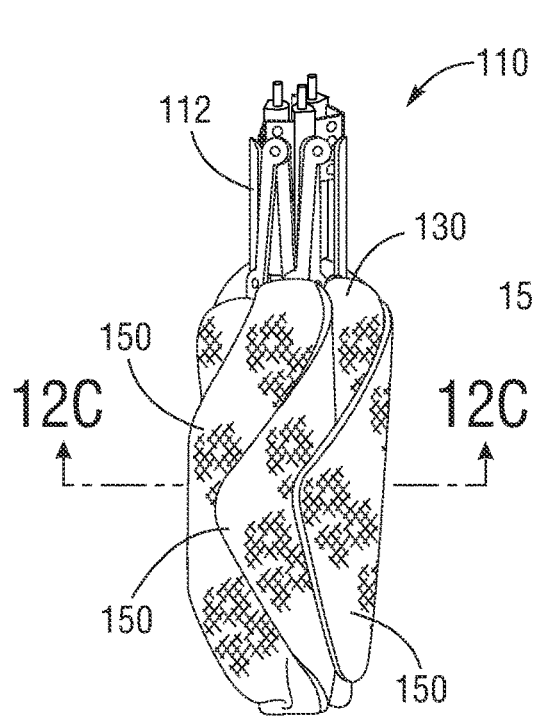
FIG. 12B shows the fully compressed prosthetic valve of FIG. 12A wherein the flaps are circumferentially folded.
Figure 12C:
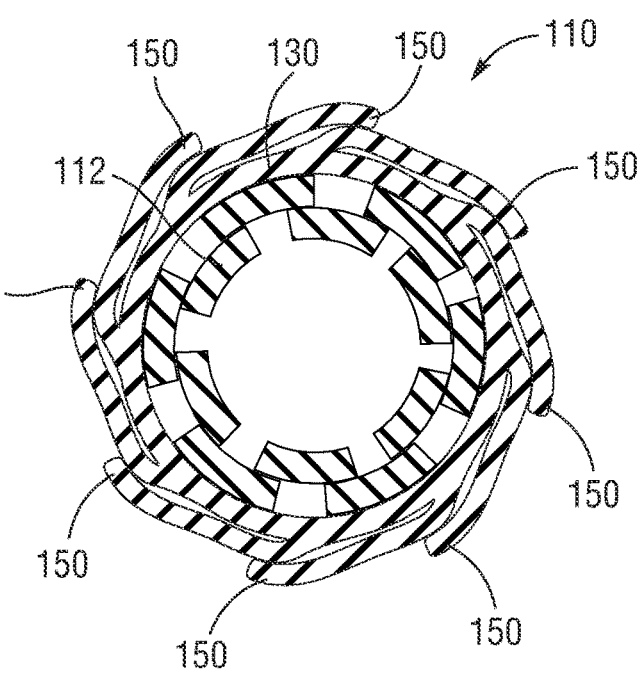
FIG. 12C shows a cross-sectional view of the fully compressed prosthetic valve depicted in FIG. 12B.

FIG. 12A shows that when the frame 112 is radially compressed, portions of the skirt 130 can billow out to form V-shaped, longitudinally extending folded flaps 150 between adjacent sections of the scallop-shaped suture line 121. In some embodiments, each flap 150 can be further folded in a circumferential direction so as to maintain a low crimping profile of the valve 110. As shown, depending on the number and size of each flap, each flap 150 can partially overlap an adjacent flap in a circumferential direction. For example, FIGS. 12B-12C show that the flaps 150 are folded in a clockwise direction (viewed from the outflow end), although it should be understood that the flaps 150 can also be folded in a counter-clockwise direction.

Figure 11:
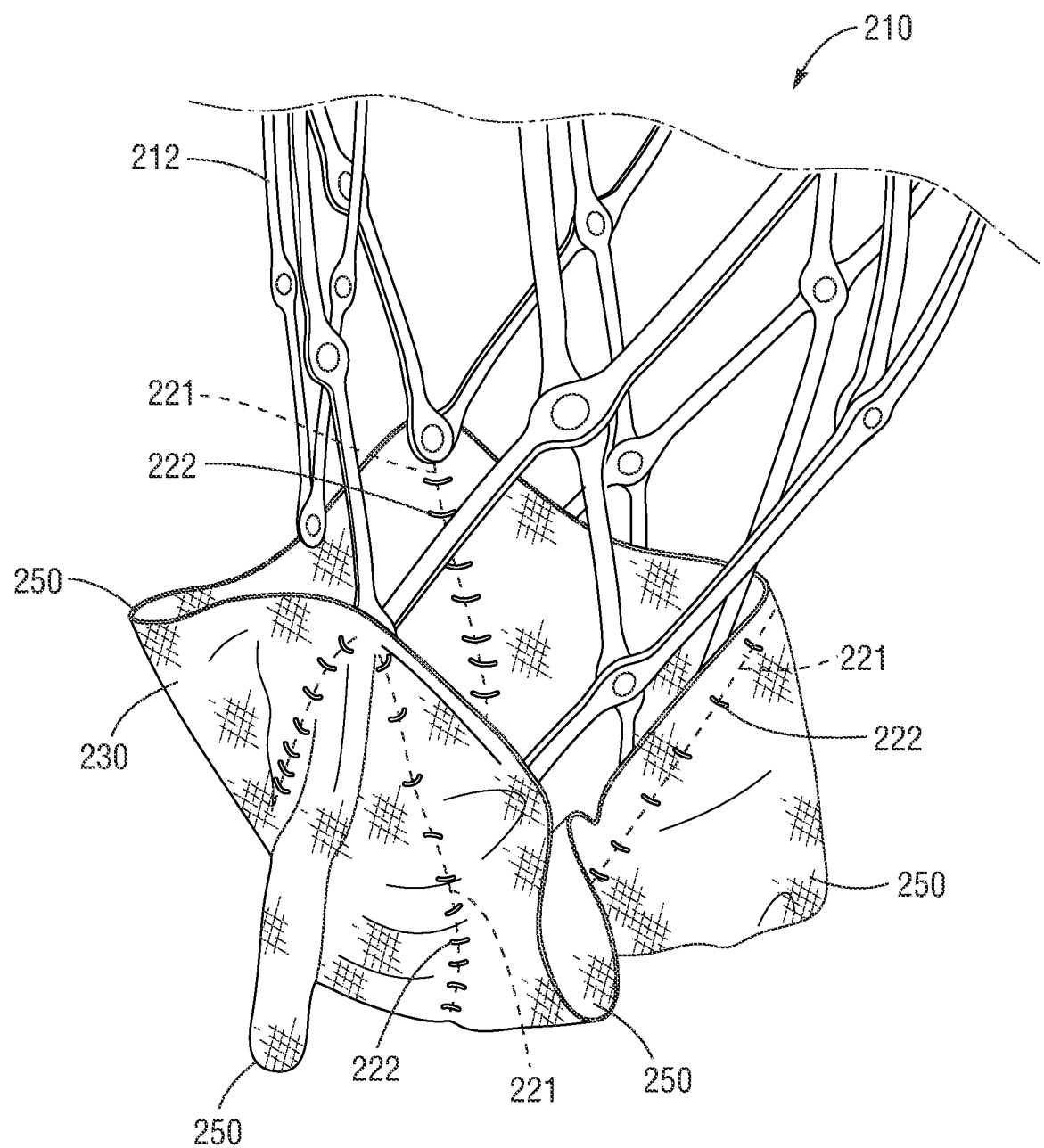
FIG. 11 shows the frame of FIG. 10 being partially compressed and the outer portion of the skirt folds outwardly.

Likewise, when the frame 212 is radially compressed, as illustrated in FIG. 11, the skirt 230 can billow out to form V-shaped, longitudinally extending folded flaps 250 between adjacent sections of the suture line 221. In order to maintain a low crimping profile, it may be desired to perform a patterned folding of the flaps 250 by wrapping the flaps 250 in a circumferential direction, similar to the embodiment illustrated in FIGS. 12B-12C.

In the illustrated embodiment, the inflow and outflow edges of the skirt 130 and skirt 230 are not connected to the frame or other components of the prosthetic valve except along the attachment line 121, 221 which forms a plurality of first V-shaped flaps opening toward the outflow end of the prosthetic valve alternating with a plurality of second V-shaped flaps opening toward the inflow end of the prosthetic valve around a circumference of the frame (as best shown in FIG. 11).

GENERAL CONSIDERATIONS

It should be understood that the disclosed embodiments can be adapted to deliver and implant prosthetic devices in any of the native annuluses of the heart (e.g., the pulmonary, mitral, and tricuspid annuluses), and can be used with any of various delivery approaches (e.g., retrograde, antegrade, transseptal, transventricular, transatrial, etc.).

For purposes of this description, certain aspects, advantages, and novel features of the embodiments of this disclosure are described herein. The disclosed methods, apparatus, and systems should not be construed as being limiting in any way. Instead, the present disclosure is directed toward all novel and nonobvious features and aspects of the various disclosed embodiments, alone and in various combinations and sub-combinations with one another. The methods, apparatus, and systems are not limited to any specific aspect or feature or combination thereof, nor do the disclosed embodiments require that any one or more specific advantages be present or problems be solved. The technologies from any example can be combined with the technologies described in any one or more of the other examples. In view of the many possible embodiments to which the principles of the disclosed technology may be applied, it should be recognized that the illustrated embodiments are only representative examples and should not be taken as limiting the scope of the disclosed technology.

Although the operations of some of the disclosed embodiments are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed methods can be used in conjunction with other methods. Additionally, the description sometimes uses terms like "provide" or "achieve" to describe the disclosed methods. These terms are high-level abstractions of the actual operations that are performed. The actual operations that correspond to these terms may vary depending on the particular implementation and are readily discernible by one of ordinary skill in the art.

As used in this application and in the claims, the singular forms "a," "an," and "the" include the plural forms unless the context clearly dictates otherwise. Additionally, the term "includes" means "comprises." Further, the terms "coupled" and "connected" generally mean electrically, electromagnetically, and/or physically (e.g., mechanically or chemically) coupled or linked and does not exclude the presence of intermediate elements between the coupled or associated items absent specific contrary language.

Directions and other relative references (e.g., inner, outer, upper, lower, etc.) may be used to facilitate discussion of the drawings and principles herein, but are not intended to be limiting. For example, certain terms may be used such as "inside," "outside,", "top," "down," "interior," "exterior," and the like. Such terms are used, where applicable, to provide some clarity of description when dealing with relative relationships, particularly with respect to the illustrated embodiments. Such terms are not, however, intended to imply absolute relationships, positions, and/or orientations. For example, with respect to an object, an "upper" part can become a "lower" part simply by turning the object over. Nevertheless, it is still the same part and the object remains the same. As used herein, "and/or" means "and" or "or", as well as "and" and "or".

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims.

We claim:

1. A prosthetic valve comprising:
    an annular frame being radially expandable and compressible between a radially compressed configuration and a radially expanded configuration, wherein the frame comprises a plurality of struts connected to each other at junctions, including a plurality of junctions defining a terminal, inflow end of the frame;
    a valvular structure positioned within the frame and configured to permit the flow of blood through the prosthetic valve in one direction and block the flow of blood in an opposing direction; and
    an annular skirt having an outer portion covering at least a portion of an outer surface of the frame and an inner portion covering at least a portion of an inner surface of the frame, wherein the skirt is folded around the inflow end of the frame so as to define a fold between the inner portion and outer portion;
    wherein the skirt is sized such that when the frame is in the expanded configuration, the outer portion of the skirt conforms to the outer surface of the frame and the junctions at the inflow end of the frame are axially spaced from the fold to form an axially extending gap between the junctions at the inflow end of the frame and the fold, and when the frame is radially compressed from the expanded configuration to the compressed configuration, the junctions at the inflow end of the frame move axially within the gap closer to the fold.

2. The prosthetic valve of claim 1, wherein the outer portion of the skirt is secured to a row of struts defining an outflow end of the frame.

3. The prosthetic valve of claim 1, wherein the outer portion of the skirt is stretched in a circumferential direction when the frame is in the expanded configuration.

4. The prosthetic valve of claim 1, wherein the skirt comprises a non-elastic fabric.

5. The prosthetic valve of claim 4, wherein the fabric is woven using polyethylene terephthalate fibers in both warp and weft directions.

6. The prosthetic valve of claim 1, wherein the skirt is woven from a first set of fibers oriented in a first direction and a second set of fibers oriented in a second direction, neither the first nor the second direction being perpendicular to the fold.

7. The prosthetic valve of claim 6, wherein the first direction is generally perpendicular to the second direction which forms an angle about 45 degrees relative to the fold.

8. The prosthetic valve of claim 1, wherein the valvular structure comprises a plurality of leaflets, each leaflet having an inflow edge portion, wherein the inflow edge portions of the leaflets define an undulating shape.

9. The prosthetic valve of claim 8, wherein the inner portion of the skirt has an undulating outflow edge sutured to the inflow edge portions of the leaflets.

10. The prosthetic valve of claim 1, further comprises a tether coupled to the skirt, wherein the tether is configured to prevent the fold from moving inside the frame when the frame is radially expanded from the compressed configuration to the expanded configuration.

11. A prosthetic valve comprising:
    an annular frame having an inflow end and an outflow end, the frame being radially expandable and compressible between a radially compressed configuration and a radially expanded configuration, wherein the frame comprises a plurality of struts connected to each other at junctions, including a plurality of first junctions defining a terminal, inflow end of the frame, and a plurality of second junctions defining a terminal, outflow end of the frame;
    a valvular structure positioned within the frame and configured to permit the flow of blood through the prosthetic valve in one direction and block the flow of blood in an opposing direction;
    an annular skirt having a fold extending around the inflow end of the frame so as to cover at least a portion of an outer surface of the frame and at least a portion of an inner surface of the frame;
    wherein when the frame is in the radially expanded configuration, an outer portion of the skirt tightly conforms to the outer surface of the frame and the first junctions at the inflow end of the frame are axially spaced from the fold to form an axially extending gap between the first junctions at the inflow end of the frame and the fold, and when the frame is in the radially compressed configuration, the first junctions at the inflow end of the frame extend axially so as to at least partially fill the axially extending gap.

12. The prosthetic valve of claim 11, wherein the valvular structure comprises a plurality of leaflets, each leaflet having an inflow edge portion, wherein the inflow edge portions of the leaflets define an undulating, curved scalloped shape that follows a plurality of interconnected strut segments of the frame along a circumferential direction when the frame is in the radially expanded configuration.

13. The prosthetic valve of claim 11, wherein the outer portion of the skirt is axially longer than the inner portion of the skirt.

14. The prosthetic valve of claim 11, wherein the outer portion of the skirt is stretched in a circumferential direction when the frame is in the expanded configuration.

15. The prosthetic valve of claim 11, further comprising a tether coupled to the skirt and extending at an oblique angle relative to a longitudinal axis of the frame such that the tether applies a tension to the skirt so as to prevent the fold from moving inside the frame when the frame is radially expanded from the compressed configuration to the expanded configuration.

16. A method of implanting a prosthetic valve mounted on a delivery apparatus, the method comprising:
    delivering the prosthetic valve in a radially compressed configuration to a target location, wherein the prosthetic valve comprises an annular frame and an annular skirt having a fold around an inflow end of the frame so as to cover at least a portion of an outer surface of the frame and at least a portion of an inner surface of the frame, wherein the frame comprises a plurality of struts connected to each other at junctions, including a plurality of junctions defining a terminal, inflow end of the frame; and
    expanding the prosthetic valve to a radially expanded configuration such that an outer portion of the skirt tightly conforms to the outer surface of the frame, and the junctions at the inflow end of the frame move axially away from the fold, thereby forming an axially extending gap between the junctions at the inflow end of the frame and the fold.

17. The method of claim 16, wherein the prosthetic valve further comprises a valvular structure having a plurality of leaflets, each leaflet having an inflow edge portion, wherein the inflow edge portions of the leaflets define an undulating, curved scalloped shape that follows a plurality of interconnected strut segments of the frame along a circumferential direction when the frame is in the radially expanded configuration.

18. The method of claim 16, wherein the outer portion of the skirt is stretched in a circumferential direction when the frame is in the expanded configuration.

19. The method of claim 16, wherein when the frame is in the radially compressed configuration, the junctions at the inflow end of the frame extend axially all the way to the fold so as to completely fill the axially extending gap.

20. The method of claim 16, wherein the prosthetic valve further comprises a tether coupled to the skirt, wherein the tether is configured to prevent the fold from moving inside the frame when the frame is radially expanded from the compressed configuration to the expanded configuration.

* * * * *